US006410297B1

(12) United States Patent
Rong et al.

(10) Patent No.: US 6,410,297 B1
(45) Date of Patent: Jun. 25, 2002

(54) PROCESSES FOR PREPARATION OF MAREK'S DISEASE VIRUS USING CONTINUOUS AVIAN CELL LINES

(75) Inventors: Sing Rong, Old Lyme; Michael G. Sheppard, North Stonington, both of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/443,800

(22) Filed: Nov. 19, 1999

Related U.S. Application Data

(60) Provisional application No. 60/111,627, filed on Dec. 9, 1998.

(51) Int. Cl.$^7$ .............................. C12N 7/00; C12N 7/08; C12N 7/02; A01N 63/00; C07H 21/02
(52) U.S. Cl. .................... 435/235.1; 435/237; 435/239; 424/93.1; 424/93.21; 424/229.1; 514/44; 536/23.1; 536/23.72; 536/27
(58) Field of Search .............................. 435/235.1, 237, 435/239, 320.1, 349, 325, 240, 172.3, 240.2; 424/229.1, 93.21, 93.1; 514/44; 536/23.1, 23.72, 27

(56) References Cited

U.S. PATENT DOCUMENTS

| | | | |
|---|---|---|---|
| 4,673,572 A | * 6/1987 | De Boer | 424/89 |
| 5,187,087 A | 2/1993 | Sondermeijer et al. | |
| 5,789,231 A | * 8/1998 | Spijkers et al. | 435/235.1 |
| 5,827,738 A | * 10/1998 | Coussens et al. | 435/349 |

FOREIGN PATENT DOCUMENTS

| | | | |
|---|---|---|---|
| EP | 0431668 B1 | | 11/1990 |
| FR | WO95/529248 | * | 11/1995 |
| WO | 9325665 | | 12/1993 |

OTHER PUBLICATIONS

Cowen and Braune 1988, Avian Diseases 1988, 32; 282–297.*
Niikura, et al.; Establishment and Characterization of a Thymidine Kinase Deficient Avian Fibroblast Cell Line Derived from a Japanese Quail Cell Line, QT35; Faculty of Veterinary Medicine; pp. 439–446 (1990).
Calnek, et al.; Diseases of Poultry, 9$^{th}$ Edition, Iowa State Press; pp. 342–285 (1991).
Silva, et al.; Monoclonal Antibody–mediated Immunoprecipitation of Proteins from Cells Infected with Marek's Disease Virus or Turkey Herpesvirus; Virol. vol. 36, pp. 307–320 (1984).
Payne; Encyclopedia of Virology; pp. 832–837 (1994).
Sonoda, et al.; Asymmetric deletion of the junction between the short unique region and the inverted repeat does not affect viral growth in culture and vaccine–induced immunity against Marek's disease; Vaccine; vol. 14, pp. 277–284 (1996).

Parcells, et al.; Retention of Oncogenicity by a Marek's Disease Virus Mutant Lacking Six Unique Short Region Genes; J. Virol. vol. 69 pp. 7888–7898 (1995).
Parcells, et al.; Characterization of Marek's Disease Virus Insertion and Deletion Mutants that Lack US1 (ICP22 Honolog), US10, and/or US2 and neighboring Short Component Open Reading Frames; Virus Genes, vol. 68, pp. 8239–8253 (1994).
Sakaguchi, et al.; Construction of Recombinant Marek's Disease Virus Type 1 (MDV1) Expressing the *Escherichia coli* lacZ gene as a possible live vaccine vector; the US10 gene of MDV1 as a stable insertion site; Vaccine vol. 12 pp. 953–957 (1994).
Reddy, et al.; Protective Efficacy of a Recombinant Herpesvirus of Turkeys as an in ovo vaccine against Newcastle and Marek's Diseases in specific–Pathogen–Free Chickens; Vaccine vol.14, pp. 469–477 (1996).
Marshall, et al.; Selection of Marek's Disease Virus recombinants Expressing the *Escherichia coli* gpt Gene; Virology, vol. 195, pp. 638–648 (1993).
Darteil, et al.; Herpesvirus of Turkey Recombinant Viruses Expressing Infectious Bursal Disease Virus (IBDV) VP2 Immunogen Induce Protection against an IBDV Virulent Challenge in Chickens; Virology, vol. 211, pp. 481–490 (1995).
Zelnik, et al.; Structure and properties of a herpes virus of turkeys recombinant which US1, US10 and ORF3 genes have been replaced by a lacZ expression cassette; Journal of General Virology; vol. 76, pp. 2903–2907 (1995).
Ross, et al.; Construction and Properties of a Turkey Herpesvirus Recombinant Expressing the Marek's Disease Virus Homologue of Glycoprotein B of Herpes Simplex Virus; J. of General Virology; vol. 74, pp. 371–377 (1993).
Sondermeijer, et al.; Avian Herpesvirus as a Live Viral Vector for the Expression of Heterologous Antigens; Vaccine vol. 11, pp. 349–358 (1993).
Morgan, et al.; Protection of Chickens from Newcastle and Marek's Disease with a Recombinant Herpesvirus of Turkeys Vaccine Expressing the Newcastle Disease Virus Fusion Protein; Avian Diseases vol. 36, pp. 858–870 (1992).
Witter, et al.; Studies on the In Vivo Replication of Turkey Herpesvirus; J. National Cancer Inst., vol. 49, pp. 1121–1130 (1972).

(List continued on next page.)

*Primary Examiner*—Mark Navarro
*Assistant Examiner*—Padma Baskar
(74) *Attorney, Agent, or Firm*—Peter C. Richardson; Paul H. Ginsburg; Jeffrey N. Myers

(57) ABSTRACT

The present invention relates to avian cell lines which efficiently support the growth and productive infection of Marek's Disease Virus at high titers. The present invention also relates to avian cell lines which have been engineered to support the growth and productive infection of recombinant Marek's Disease Virus at high titers. The present invention relates a process for the preparation of Marek's Disease Virus in quantities suitable for vaccine purposes.

11 Claims, 7 Drawing Sheets

OTHER PUBLICATIONS

Edison, et al.; Detection of Marek's Disease Antigen in Feather Follicle Epithellum of Chickens Vaccinated Against Marek's Disease; J. National Cancer Inst., vol. 47, pp. 113–120 (1971).

Ogura, et al.; Establishment and Characterization of a Virus–free Chick Cell Line; Acta Med. Okayama, vol. 41, pp. 141–143 (1987).

Abujoub, et al.; Development of a Sustainable Chick Cell Line Infected with Marek's Disease Virus; Virology, vol. 214, pp. 541–549 (1995).

Nazeria; An Updated List of Avian Cell Lines and Transplantable Tumours; Avian Pathology, vol. 16, pp. 527–544 (1987).

Kopta, C. and J.H. Steinbach, "Comparison of Mammalian Adult and Fetal Nicotinic Acetylcholine Receptors Stably Expressed in Fibroblasts," J. Neurosci. (Jun. 1994) 14(6):3922–3933.

Coutinho, L.L., et al. "Development somite formation in a quail line exhibiting myofiber hyperplasia is accompanied by delayed expression of myogenic regulatory factors and myosin chain," Development (1993) 117:563–569.

Rossi, S.G. and R.L. Rotundo, "Cell Surface Acetylcholinesterase Molecules on Multinucleated Myotubes are Clustered over the Nucleus of Origin," J. Cell. Biol. (Dec. 6, 1992) 119(6):1657–1667.

Jaffredo, T. et al., "MC29–Immortalized Clonal Avian Heart Cell Lines Can Partially Differentiate in Vitro," Exper. Cell Res. (1991) 192:481–491.

Antin, P.B. and C.P. Ordahl, "Isolation and Characterization of an Avian Myogenic Cell Line," Dev. Biol. (1991) 143:111–121.

* cited by examiner

PROCESSES FOR PREPARATION OF MAREK'S DISEASE VIRUS USING CONTINUOUS AVIAN CELL LINES

CROSS REFERENCE TO RELATED APPLICATIONS

This application claims the benefit of U.S. Provisional Application No. 60/111,627, filed Dec. 9, 1998.

INTRODUCTION

The present invention relates to the use of continuous avian cell lines that support the growth and productive infection of Marek's Disease Virus (MDV) at high titers. The present invention relates to a cell line that can be used as a substrate to efficiently propagate large quantities of Marek's disease virus, in particular, for vaccine production. The present invention relates to recombinant Marek's disease viral vectors and cell lines to package said vectors and recombinant Marek's disease viruses which may be used as vaccines. Marek's Disease Virus vectors and vaccines may be used to protect avians from infection with Marek's Disease Virus and against disease resulting from infection.

BACKGROUND OF THE INVENTION

Marek's Disease (MD) is an acutely oncogenic disease of chickens, which causes lymphomas, visceral tumors, nerve lesions and immunosuppression. The disease is global and ubiquitous in distribution. The etiologic agent is a herpesvirus, Marek's Disease Virus. Marek's Disease has been a primary cause of deaths and condemnations in broiler flocks [Calnek, B. W. and Witter, R. L., Diseases of Poultry, 9th edition, Iowa State Press, Ames, Iowa, pp. 342–385 (1991)].

There are three serotype of Marek's Disease Virus. Serotype 1 includes all pathogenic strains and their attenuated derivatives. Serotype 2 consists of naturally avirulent chicken viruses, while serotype 3, also known as Herpesvirus of Turkeys (HVT), includes avirulent turkey viruses that are capable of replication in chickens. The three serotypes are partially cross-protective, but can be distinguished using polyclonal or monoclonal antibody tests, polypeptide patterns and DNA analysis (Silva, R. F. and Lee, L. F., Virol. vol. 36, pp. 307–25 320 (1984); Payne, L. N., in "Encyclopedia of Virology" Edited by Webster, R. G. & Granoff, A., pp. 832–838 (1994)) and other known methods.

The DNA genome of MDV serotype 1 and HVT are linear double-stranded molecules of approximately 180 and 167 kilobases, respectively. Similar to other herpes viruses, the genome of MDV consists of a long unique region (UL) and a short unique region (US) surrounded by inverted repeats. The genomes of the three MDV serotypes are in the form of full length closed circular DNA, however there is little homology between the three serotypes of MDV under stringent hybridization conditions even though their genomes are colinear [see Payne, L. N., in "Encyclopedia of Virology" edited by Webster R. G. and Granoff A., pp. 832–838 (1994)].

Marek's Disease Virus appears to be less recombinogenic than other herpesviruses, and the cell-associated nature of the virus makes plaque purification of recombinants away from parental virus problematic. Nevertheless, recombinant MD viruses have been generated from serotype 1 [Sonoda, K. et al., Vaccine V. 14, pp. 277–284 (1996); Parcells, M. S., et al., J. Virol., V. 69, pp. 7888–7898 (1995); Parcells M. S., et al., Virus Genes, V. 9, pp. 5–13, (1994Parcells, M. S., et al., J. Virol., V. 68, pp. 8239–8253 (1994); Sakaguchi, M., Vaccine V. 12, pp. 953–957 (1994); Reddy, S. K., et al., Vaccine V. 14, pp. 469–477 (1996)], serotype 2 [Marsha D. R., et al., Virol. V. 195, pp. 638–648 (1993); Silva, R. F., 14th International Herpesvirus Workshop (Abstract) (1989)]; and serotype 3 [Reddy, S. K., et al., Vaccine V. 14, pp. 469–477 (1996); PCT Parent Application WO 95/29248 (1995); Silva, R. F., 14th International Herpesvirus Workshop (Abstract) (1989); Darteil, R., et al., Virol. V. 211, pp. 481–490 (1995); U.S. Pat. No. 5,187,087 issued in 1995; Zelnik, V., et al., J. Gen. Virol. V. 76, pp. 2903–2907 (1995); PCT Patent Application WO 93/25665, published (1993); Ross, L. J. N., et al., J. Gen. Virol., V. 74, pp. 371–377 (1993), Sondermeijer, P.J.A., et al., Vaccine V. 11, pp. 349–358 (1993); European Patent No. 431,668 B1, published (1995); Morgan, R. W., et al., Avian Dis., V. 36, pp. 858–870 (1992); Bandyopadhyay, P. K., et al., 13th International Herpesvirus Workshop 323 (Abstract) (1988)]. In all of the above mentioned references, the viruses were replication competent and were produced in primary avian cells.

Commercially available Marek's Disease Virus vaccines, with the exception of some monovalent HVT formulations, consist largely of live Marek's Disease Virus-infected primary chicken embryo fibroblast (CEF) cells. A significant problem associated with using whole live Marek's Disease Virus-infected primary chicken cells to grow Marek's Disease Virus for use in vaccines is that the CEF cells must be stored at liquid nitrogen temperatures and administered by injection in order to be effective. Whole live cell vaccines have been previously necessary since the three Marek's Disease Virus serotypes are strongly cell-associated in cell culture and in most tissues of an infected bird. Spread of infection within birds can be achieved by direct cell to cell contact, with little or no cell-free virus being released. Infectious virions are produced only in the feather follicle epithelium (FFE), and are responsible for bird-to-bird transmission [Calnek, B. W., et al., Avian Dis., V. 14, pp. 219–233 (1970); Witter, R. L., et al., J. Natl. Cancer Inst., V. 49, pp. 1121–1130 (1972); Edison, C. S., et al., J. Natl. Cancer Inst., V. 47, pp. 113–120 (1971)].

Commercial cell-free Marek's Disease Virus vaccines can be made by cell culture. However, the production of cell-free Marek's Disease Virus vaccines has been thus far been limited to vaccines produced using only serotype 3 Marek's Disease Virus. This is because only serotype 3 Marek's Disease Virus makes free virions in sufficient quantities for production of Marek's Disease Virus vaccines. It has been suggested that lack of expression of the viral glycoprotein D (gD) gene may be involved in limiting release of cell-free virions [PCT Patent Application WO 95/29248 published (1995); Tan, X. and Velicer, L. F., 18th International Herpesvirus Workshop A, 145 (Abstract) (1993)].

In addition to CEF, other primary avian cells have been used to grow Marek's Disease Virus, including chicken embryo kidney (CEK) and duck embryo fibroblast (DEF). A chemically transformed quail cell line designated QT35 has been described as a substrate for avirulent serotypes 2 and 3 of Marek's Disease Virus, but not serotype 1. [Nikura, M., Nanta, T. et al., J. Vet. Med. Sci., V. 53, pp. 439446 (1991)]. A chemically transformed CEF cell line designated CHCC-OU2 [Ogura, H. and Fujiwara, T., Acta Med. Okayama, V. 41, pp. 141–143 (1987)] has been described as supporting the growth of Marek's Disease Virus-1 [Abujoub, A.3 and Coussens, P. M., Virol., V. 214, pp. 541–549 (1985)].

Other known processes for producing Marek's Disease Virus include the use of tumorigenic or oncogenic cell lines.

Marek's Disease Virus-transformed lymphoblastoid cell lines [Nazerian, K. Avian Pathol. V. 16, pp. 527–544 (1987)] are derived from lymphoid tumors in chickens infected with oncogenic Marek's Disease Virus-1. The viral genome is maintained in a latent or semi-latent state in these cells, such that transmission of infection to co-cultivated CEF cells or DEF cells occurs at a low frequency, if at all. In addition, these lymphoblastoid lines are refractory to superinfection with other Marek's Disease Virus viruses. Furthermore, Marek's Disease Virus-transformed lymphoblastoid cell lines have not demonstrated utility in the production of nonrecombinant (conventional) Marek's Disease Virus vaccines or in the preparation of recombinant Marek's Disease Virus viruses or genetically altered Marek's Disease Virus viruses or vectors.

Similarly, lymphoblastoid cell lines [Nazerian, K., Avian Pathol., V. 16, pp. 527–544 (1987)] derived from oncogenic avian retroviruses (avian leukosis virus and reticuloendotheliosis virus) are not useful for the production of commercial Marek's Disease Virus vaccines or for the generation of recombinant Marek's Disease Virus, due to the shedding of retroviruses, the poor growth characteristics of lymphoblastoid cells, and the low level of productive Marek's Disease Virus infection. Thus, there still remains a need for a suitable substrate to grow Marek's Disease Virus to high titers for vaccine purposes.

SUMMARY OF THE INVENTION

Figure 1:
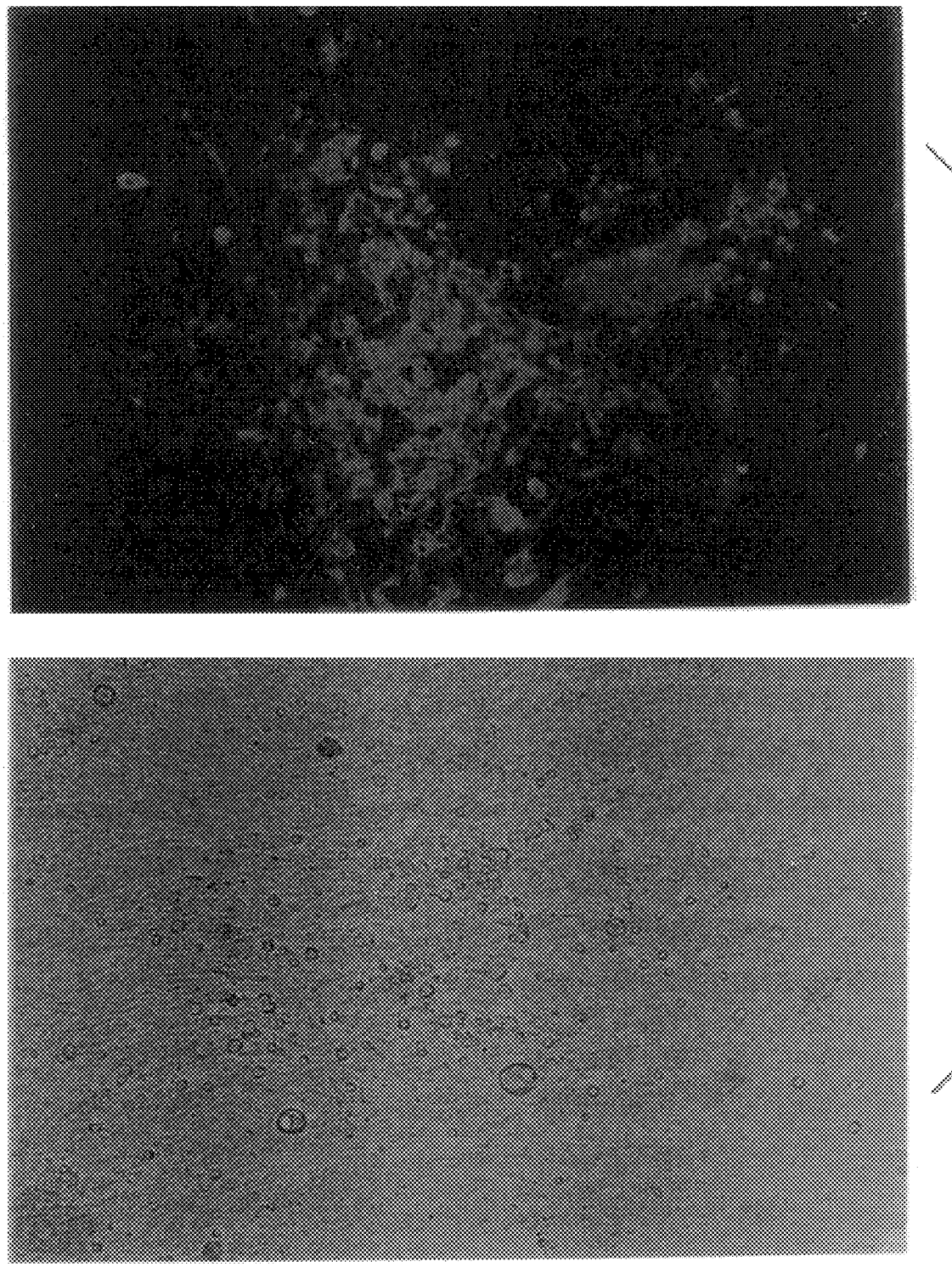
FIG. 1 describes the immunofluoresence and CPE (cytopathic effect) of MDV-1 (652)/QM7 infected foci. QM7 cells were infected with 652/DEF for 7 days in DMEM/F-12 with 3% FBS (fetal bovine serum). The infected cells were then fixed with 80% acetone and stained with MDV-1 specific monoclonal antibodies (anti-gB and anti-pp38). The negative control, QM7 co-cultivated with DEF, stained completely negative. Upper panel immunofluoresence of 652/QM7 foci; Lower panel, CPE of 652/QM7 infected foci.
Figure 2:
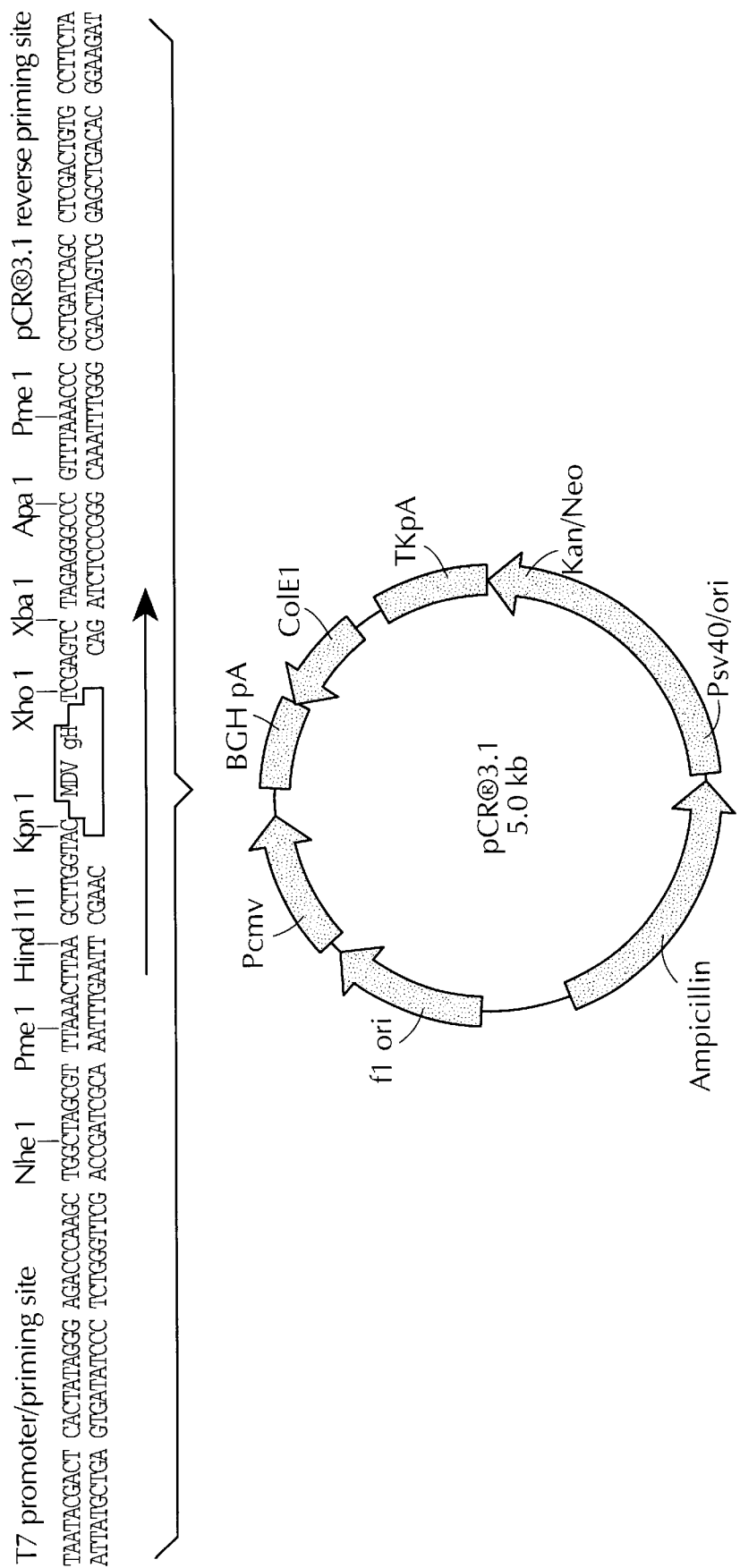
FIG. 2 is a map of the pCR 3.1 (SEQ ID NOS: 7–8) vector containing the insertion of the Marek's disease virus gH gene. The 2.6 kb gH gene of MDV-1 was cloned from Md5 strain by PCR method. It was then cloned into the multiple cloning site of pCR3.1 vector (Invitrogen Inc., catalog number K3000–01).
Figure 3:
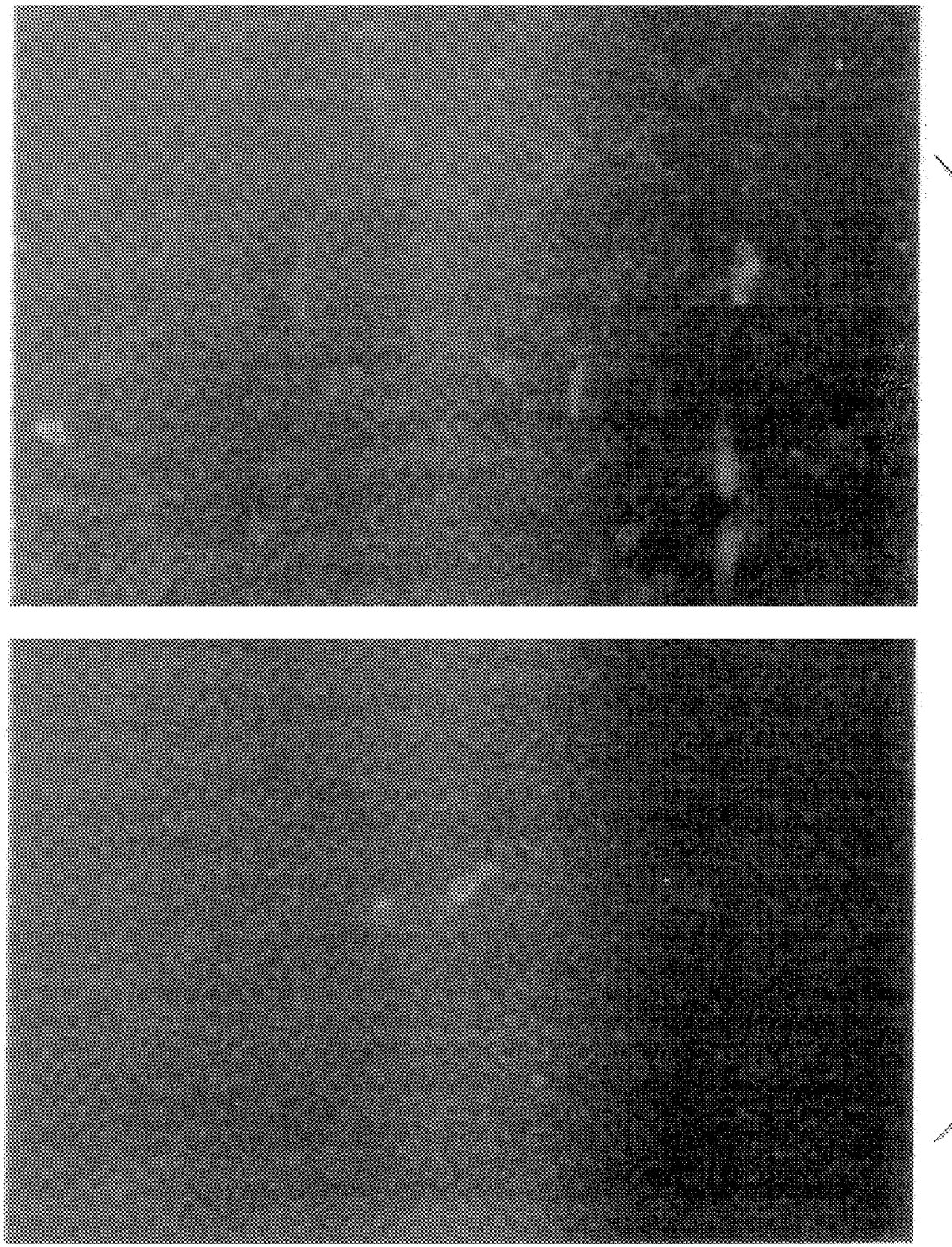
FIG. 3 describes the immunofluoresence detection of MDV-1 gH and gD proteins. QM7 cells were transfected with pCR3gH-HA and pCR3gD-HA (the gH and gD genes with an HA tag), respectively. The transfected cells were fixed 48 hours later with 80% acetone and stained with monoclonal antibody against HA (Babco Mab, catalog number MMS-101R). Panel A, gH-HA in QM7 cells; Panel B, gD-HA in QM7 cells.
Figure 4:
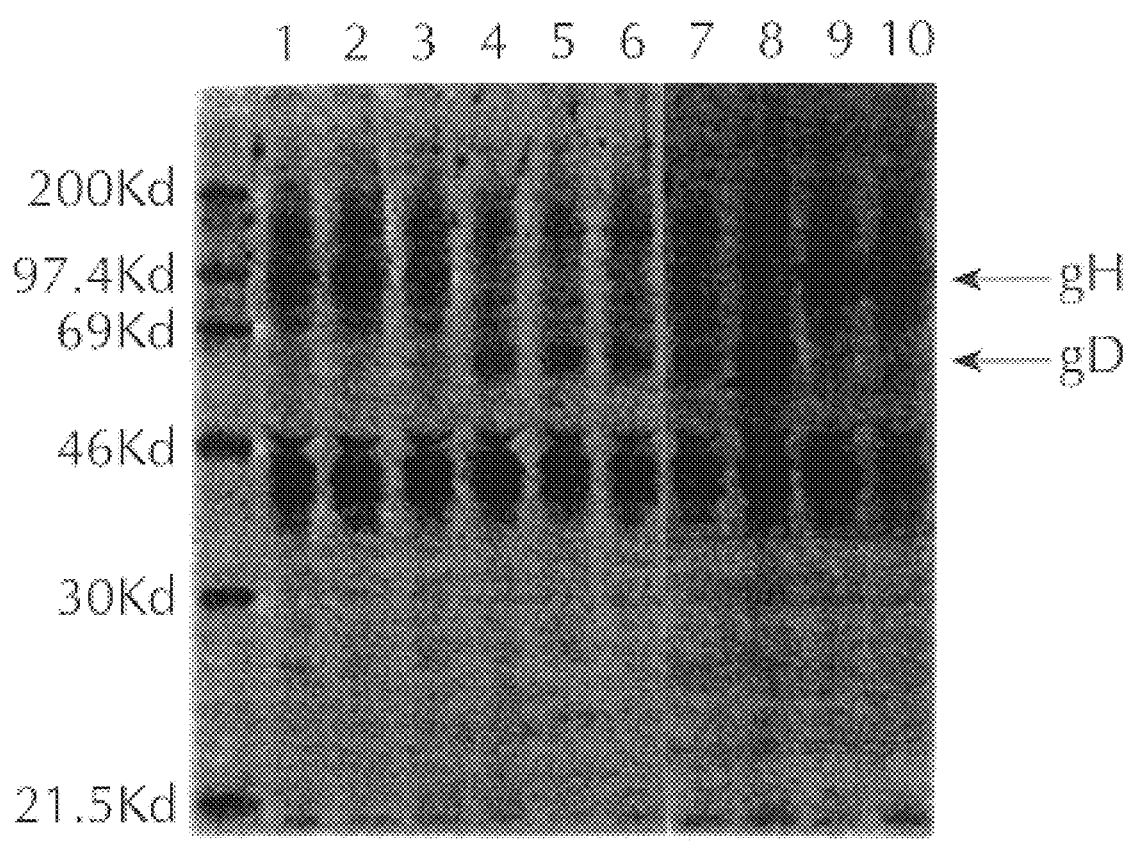
FIG. 4 describes the immunoprecipitations analysis of MDV-1 gH and gD proteins. QM7 cells were stably transfected with pCR3gH-HA and pCR3gD-HA (gH and gD genes with an HA tag), respectively. G418 resistant cells were selected and cloned. These cells were then metabolically labeled with 35S-Met (TransLabel, ICN) for 5 hours and lysed in lysis buffer (Boeringer Mannheim immunoprecipitation kit). Protein G sepharose was used after incubating with monoclonal antibody against HA (Babco Mab, catalog number MMS-101 R). Lanes 1–3, pools of G418 resistant cells transfected with pCR3gH-HA; Lanes 4–6, pools of G418 resistant cells transfected with pCR3gD-HA; Lanes 7 and 8, single cells clones of gH-HA expressing cells; Lanes 9 and 10, single cells clones of gD-HA expressing cells.
Figure 5:
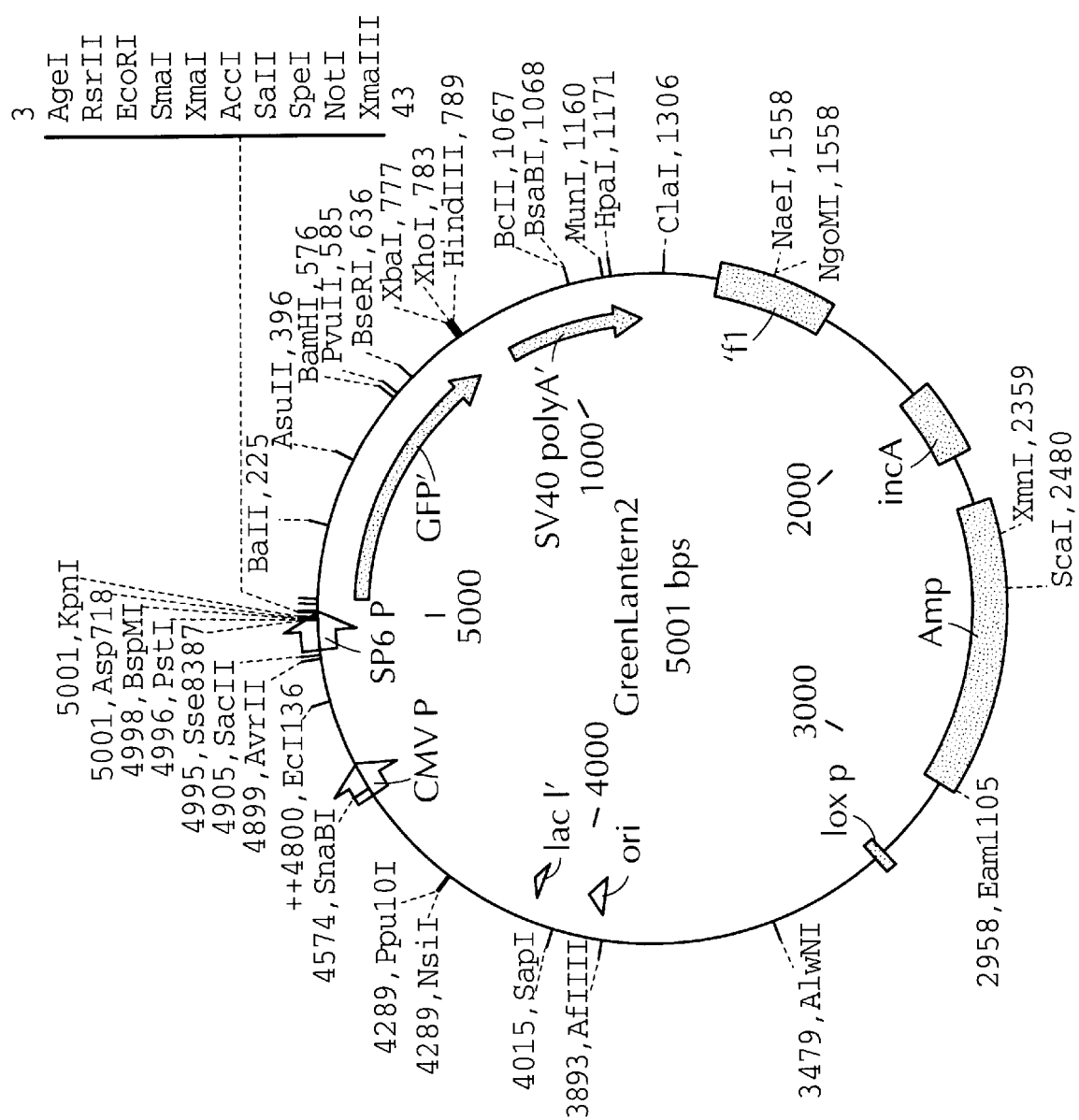
FIG. 5 is a map of the pGreenLantern2 plasmid (Life Technologies).
Figure 6:
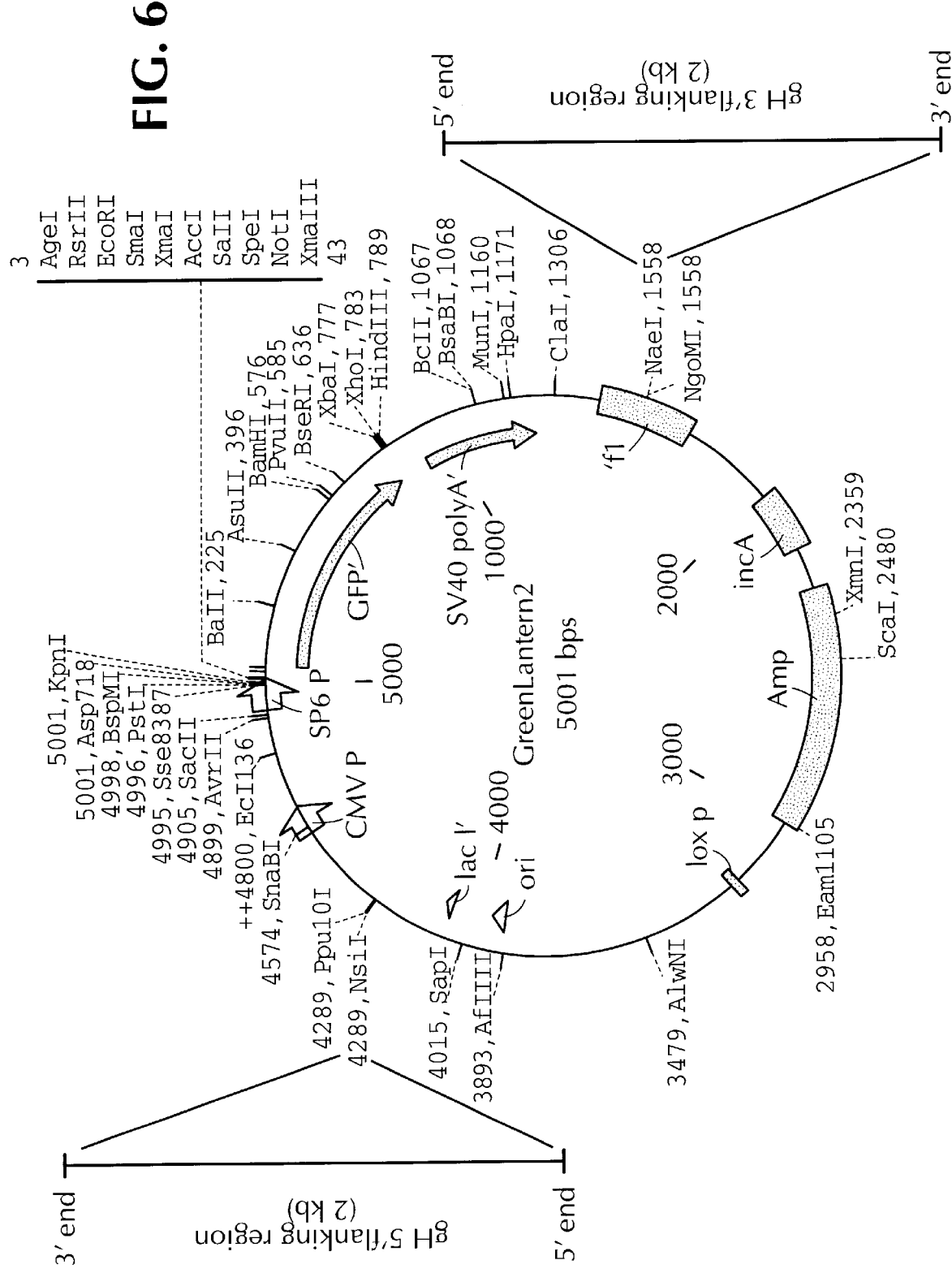
FIG. 6 is a map of the pGL2/5'–3'gfp plasmid. In this plasmid, 2 kb length of MDV-1 (Md5)5'gH flanking region was inserted into the revised Nsi I Site of pGreenLantern2, and 2 kb length of MDV-1 (Md5) 3'gH flanking region was inserted into the Nae I site of pGreenLantern2.
Figure 7:
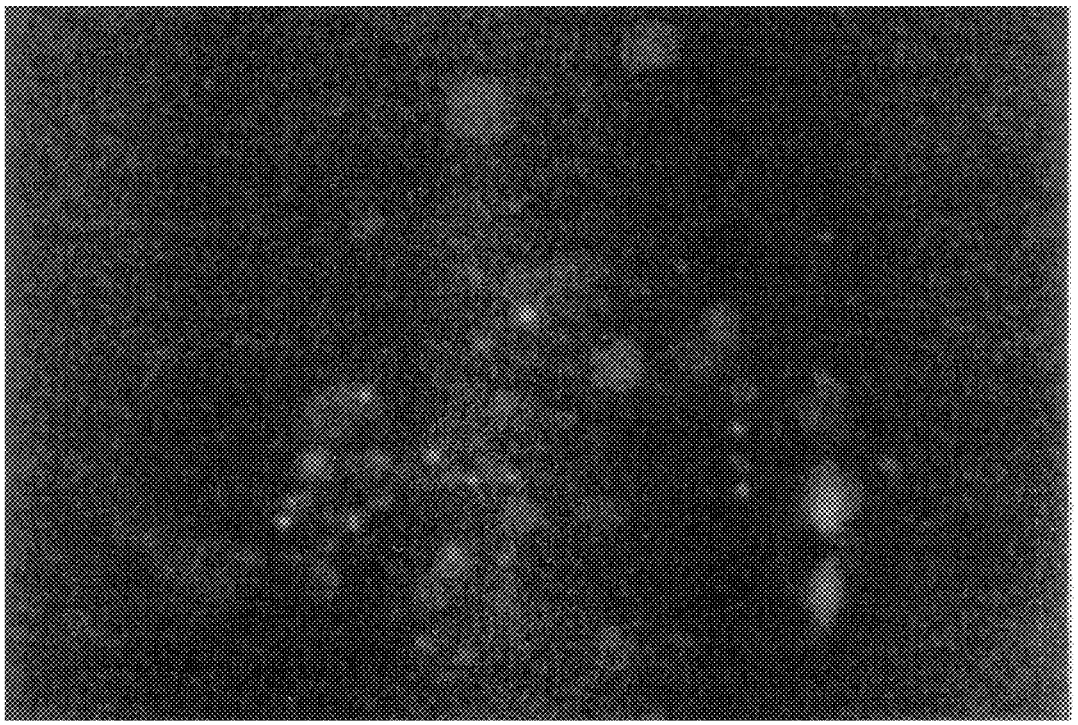
FIG. 7 describes the identification of gfp+recombinant MDV-1 virus. Plasmid pGH2/5'–'3 was transfected into 652/QM7 infected cells. Cells were passaged twice when the cytopathic effect of the viral infection was clearly visible. Cell suspension was then passed through FACS sorter for its green fluoresent protein expression. The gfp+sorted cells were plated onto a 12-well pate. Upper panel, gfp+infected foci were visualized under u.v. light; Lower panel, the same foci under regular light owing viral CPE.
Figure 7:
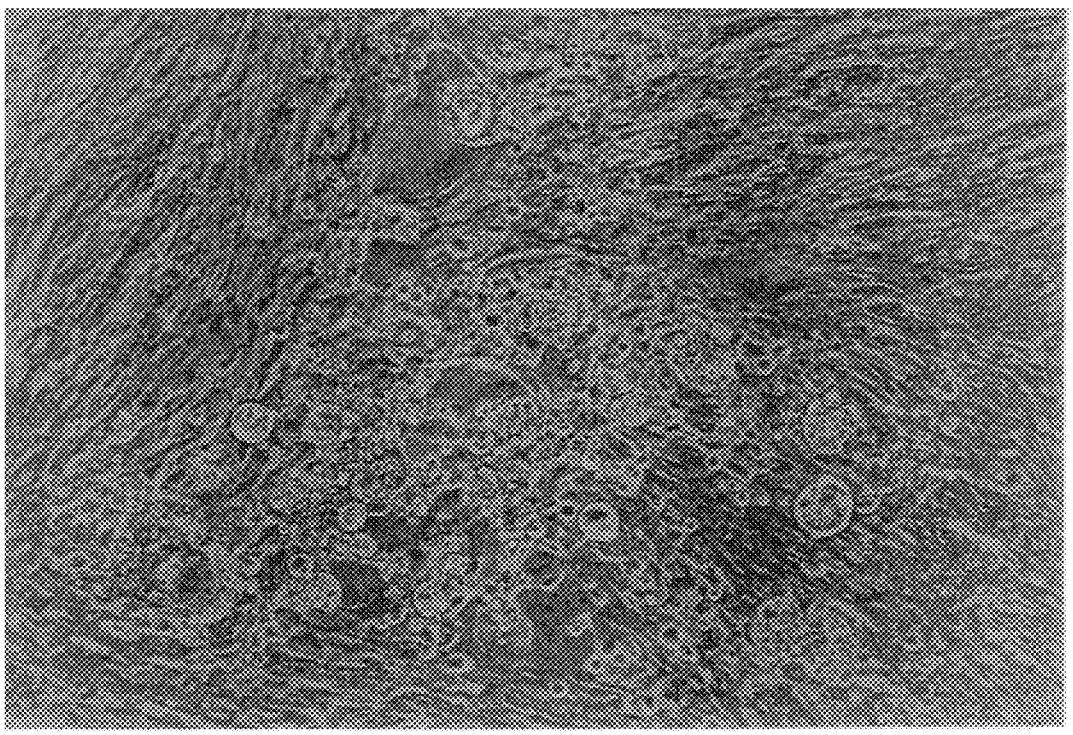

The present invention relates to avian cell lines that efficiently support the growth and productive infection of Marek's Disease Virus (MDV) at high titers. The present invention also relates to avian cell lines that have been engineered to support the growth and productive infection of both naturally occurring and recombinant Marek's Disease Virus at high titers. The present invention relates to a process for the preparation of Marek's Disease Virus in quantities suitable for vaccine purposes.

The present invention is based, in part, on the discovery of continuous avian cell lines that support the growth and productive infection of Marek's Disease Virus at high titers. In particular, it has been discovered that the avian cell line that supports viral growth at high titers is a quail muscle myoblast cell line.

In accordance with the present invention, the term "MDV" refers to an MDV viral particle that corresponds to a naturally occurring MDV viral particle, e.g., a wildtype MDV or a naturally occurring mutant MDV, or a recombinant MDV viral particle. A naturally occurring MDV viral particle is encoded by a wildtype MDV genome or the genome of a naturally occurring MDV. A recombinant MDV viral particle is encoded by a recombinant MDV genome. A recombinant MDV genome comprises the nucleotide sequences of the MDV genome or a fragment thereof. Such fragment must be of sufficient length so as to encode at least one MDV gene product or a fragment of such gene product such that the fragment of the gene product retains the activity of the gene. For example, the recombinant MDV genome comprises the nucleotide sequence of MDV that has been deleted of a gene(s) whose gene product is essential for viral replication or some other state of the viral life cycle. In addition, a recombinant MDV genome can further comprise a nucleotide sequence that encodes a heterologous gene or heterologous fragment. Such fragment comprises nucleotide sequences encoding an antigenic epitope, e.g., epitopes of avian leukosis virus (ALV), a regulatory sequence, e.g., a promoter sequence, or a fragment of a gene that still retains a sufficient fragment such that the polypeptide encoded by such fragment retains the activity of the gene product.

The present invention encompasses continuous avian cell lines that contain DNA encoding naturally occurring MDV or a recombinant MDV, e.g., nucleotide sequence of MDV or DNA encoding the nucleotide sequence of MDV under the control of a heterologous regulatory element, or DNA encoding the nucleotide sequence of MDV containing at least one heterologous gene or fragment thereof. In a preferred embodiment, the present invention also encompasses quail cell lines that have been engineered to express naturally occurring MDV or a recombinant MDV.

The present invention also encompasses a continuous avian cell line that is transfected with DNA encoding the nucleotide sequence of MDV that has been deleted of a gene or fragment thereof which gene product is essential for viral replication or some other stage of the viral life cycle. In yet another embodiment, the present invention encompasses continuous avian cell lines which contain and express DNA encoding the MDV gene or fragment thereof which is essential for viral replication or some other stage of the viral life cycle. Such nucleotide sequences may be expressed constitutively or transiently under the control of the cell's own regulatory elements or heterologous regulatory elements. The present invention further encompasses continuous avian cell lines which are engineered to stably express the nucleotide sequences of MDV or a fragment thereof, either under the control of constitutively active regulatory elements or inducible regulatory elements.

The present invention also encompasses continuous avian cell lines that are infected with naturally occurring MDV or recombinant MDV, or a cell lysate or components of cells infected with MDV.

The MDV may be selected from the group consisting of serotype 1, serotype 2, serotype 3, taken singly or in any combination thereof.

In another aspect, the invention relates to the use of MDV for the preparation of a vaccine capable of inducing protection against disease in avians.

Preferably, the continuous avian cell line used is a quail cell line, such as the QM7 cell line designated ATCC-CRL 12599 with the American Type Culture Collection, 10801 University Blvd., Manassas Va. 20110–2209 on Nov. 24, 1998, which may be infected with the 652 strain of MDV, such as the 652-QM7 cell line designated ATCC-CRL 12600, deposited with the American Type Culture Collection, 10801 University Blvd., Manassas Va. 20110–2209 on Nov. 24, 1998. In a preferred embodiment, the present invention does not encompass the use of the chemically transformed quail cell line designated QT35 to culture MDV serotypes 2 or 3.

The present invention also encompasses a method for propagating MDV that comprises introducing naturally occurring MDV or a recombinant MDV to a continuous avian cell line by infecting the cell line with MDV, or cells infected with MDV or cell lysates thereof, and culturing the infected cell line and harvesting cell components therefrom. The invention further encompasses formulating a vaccine from said cells or components thereof capable of inducing protection against disease in avians.

The present invention also encompasses a method of propagating MDV that comprises infecting a continuous avian cell line with DNA which encodes the nucleic acid sequence of a naturally occurring MDV or a recombinant MDV, culturing the cell line and harvesting components therefrom. In accordance with this aspect of the invention, the DNA may encode the nucleotide sequence of a naturally occurring MDV; the nucleotide sequence of recombinant MDV which comprises the nucleotide sequences of the MDV genome or a fragment thereof. Such fragment must be of sufficient length so as to encode at least one MDV gene product or a fragment of such gene product such that the fragment of the gene product retains the activity of the gene. In addition, the recombinant MDV may be operatively linked to a heterologous regulatory element, or may contain at least one heterologous gene or fragment.

The present invention also encompasses a continuous avian cell line that is transfected with DNA encoding the recombinant MDV that has been deleted of a gene or fragment thereof which gene product is essential for viral replication or some other stage of the viral life cycle. In yet another embodiment, the present invention encompasses continuous avian cell lines that contain and express DNA encoding the MDV gene or fragment thereof which is essential for viral replication or some other stage of the viral life cycle. Such nucleotide sequences may be expressed constitutively or transiently under the control of the cell's own regulatory elements or heterologous regulatory elements. Such cell lines may be used to produce recombinant MDV by infecting and culturing such an engineered avian cell line with DNA encoding the nucleic acid sequence of Marek's Disease Virus. For example, the deleted gene can be one essential for replication. More particularly, the deleted gene can be the gH gene of Marek's Disease Virus or a fragment(s) thereof. In accordance with another embodiment of the present invention, second generation MDV may be produced by infecting and culturing an avian cell line with a cell lysate or components thereof obtained from cells infected with MDV or engineered to express MDV.

In accordance with the present invention the avian cell lines may be engineered to transiently express the DNA encoding naturally occurring or recombinant MDV or may be engineered to stably express the DNA encoding naturally occurring or recombinant MDV. In another preferred embodiment of the present invention, the avian cell line is a quail muscle myoblast cell line.

The MDV can be selected from the group consisting of serotype 1, serotype 2 and serotype 3, taken singly, or in any combination thereof.

In another aspect the invention relates to the above described method wherein the MDV is a virus used for the preparation of a vaccine capable of inducing protection against disease in avians.

Preferably, the continuous avian cell line used is a quail muscle myoblast cell line infected with the 625 strain of MDV, such as cell line ATCC No. ATCC-CRL 12599 as deposited with the ATCC on Nov. 24, 1998. Examples of other suitable strains include the MDV-1 strains 584A and Md5. MDV-1 strain 652 may be obtained from quail myoblast cells infected with the 652 strain as deposited with the ATCC on Nov. 24, 1998, designated ATCC No. ATCC-CRL 12600.

The invention relates to generating a safe attenuated MDV-1 recombinant to use as a vaccine, to alter the extreme cell-associated nature of the MDV-1 virus in order to render it cell-free and to generating a continuous cell line to produce the virus.

In another embodiment, the present invention relates to engineering recombinant Marek's Disease Viruses and viral vectors for the use as vaccines. In yet another embodiment, the invention relates to recombinant Marek's Disease viral vectors and viruses which are engineered to encode mutant Marek's Disease viral genes or to encode combinations of genes from serotypes of Marek's Disease Virus.

The expression products and/or chimeric virions obtained may advantageously be utilized in vaccine formulations. The expression products and chimeric virions of the present invention may be engineered to create vaccines against a broad range of pathogens which afflict avians, including viral antigens. In particular, the chimeric virions of the present invention may be engineered to create anti-ALV (avian leukosis virus) vaccines, wherein an immunogenic polypeptide from ALV, is engineered into the genome of MDV to construct a vaccine that is able to elicit immune responses to both MDV and ALV. In addition, heterologous gene sequences that can be constructed into the chimeric vectors of the invention for use in vaccines include, but are not limited to, sequences derived from other serotypes of MDV, New Castle Disease Virus (NDV), Infectious Bursal Disease Virus (IBDV), Infectious Bronchitis Virus (IBV), Chicken Anemia Virus (CAV), Infectious Laryngotracheitis Virus (ILV), Reticuloendotheliosis Virus (RV) and Avian Influenza Virus (AIV) (see, Fields et al. (ed.), 1991, Fundamental Virology, Second Edition, Raven Press, New York, incorporated by reference herein in its entirety).

The vaccine can be comprised of MDV selected from the group consisting of serotype 1, serotype 2 and serotype 3, taken either singly or in any combination thereof. Preferably, the vaccine is produced using a avian cell line infected or transfected with Marek's Disease Virus.

Still another aspect of the invention is a recombinant MDV produced using the above mentioned method. The recombinant MDV can, for example, comprise the nucleic acid sequence of naturally occurring MDV from which one or more genes has been deleted, such as a gene essential for viral replication. An example of such an essential gene is the glycoprotein H (gH) gene, or fragment thereof, of the MDV genome. The resulting disabled (replication defective) virus is infectious for a single cycle provided that a complementary cell line, genetically engineered to contain the gene essential for viral replication and thereby the expression product of the deleted gene, is available to propagate the disabled virus. The production of disabled viruses and their use as vaccines is described in PCT Application GB91/01632 (Publication No. WO 92/05263), which is incorporated herein in its entirety.

Yet another aspect of the present invention is a cell line that comprises a genetically engineered avian cell line, which is capable of expressing a gene of naturally occurring MDV that is essential for replication, such as for example, gH, and that is capable of replication of disabled MDV virus.

Yet another aspect of the invention is a MDV vector produced using the method described above. The MDV vector comprises recombinant MDV and one or more heterologous genes or fragment(s) thereof. Optionally, the MDV vector has a 3' flanking region comprising a nucleic acid sequence as described in SEQ ID NO: 2. Also optionally, the MDV vector can have a 5' flanking region comprising a nucleic acid sequence as described in SEQ ID NO: 1. Furthermore, the MDV vector can have both a 3' flanking region comprising a nucleic acid sequence as described in SEQ ID NO 2 and a 5' flanking region comprising a nucleic acid sequence as described in SEQ ID NO: 1.

Yet another aspect of the invention relates to a method for protecting animals against disease by administering to such animals a vaccine comprising MDV produced by the method described above. Preferably, the animal is avian.

DETAILED DESCRIPTION OF THE INVENTION

The present invention provides processes for the use of continuous avian cell lines for the production of naturally occurring and recombinant Marek's Disease Virus (MDV), the production of genetically engineered MDV and MDV vectors, continuous avian cell lines infected or transfected with MDV and vaccines capable of protecting animals against disease by MDV and/or other disease causing agents produced using such processes. Also, provided are methods of administrating MDV vaccines and MDV vector-produced vaccines to animals for protection against infection by MDV.

The preparation of the MDV vaccines of the present invention may be divided into the following stages solely for the purpose of description and not by way of limitation: (a) construction of recombinant MDV templates; (b) engineering avian cell lines to support productive infection of naturally occurring and recombinant MDV; and (c) rescue of MDV, cell cultures, lysates or components of lysates to be formulated as vaccines. The present invention also encompasses vaccine formulation comprising the nucleotide sequences encoding recombinant MDV. For clarity of discussion, the invention is described in the working Examples using MDV strain 652 serotype 1; however, any serotype of MDV may be utilized.

In accordance with the present invention, the term 'MDV' refers to an MDV viral particle that corresponds to a naturally occurring MDV viral particle, e.g., a wildtype MDV or a naturally occurring mutant MDV, or a recombinant MDV viral particle. A naturally occurring MDV viral particle is encoded by a wildtype MDV genome or the genome of a naturally occurring MDV. A recombinant MDV viral particle is encoded by a recombinant MDV genome. A recombinant MDV genome comprises the nucleotide sequences of the MDV genome or a fragment thereof. Such fragment must be of sufficient length so as to encode at least one MDV gene product or a fragment of such gene product such that the fragment of the gene product retains the activity of the gene. For example, the recombinant MDV genome comprises the nucleotide sequence of MDV that has been deleted of a gene(s) whose gene product is essential for viral replication or some other state of the viral life cycle. In addition, a recombinant MDV genome can further comprise a nucleotide sequence that encodes a heterologous gene or a heterologous fragment. Such fragment comprises nucleotide sequences encoding an antigenic epitope, a regulatory sequence, or a fragment of a gene that still retains a sufficient fragment such that the polypeptide encoded by such fragment retains the activity of the gene product. MDV also includes recombinantly produced Marek's Disease virus (recombinant Marek's Disease Virus) or a fragment thereof.

The present invention encompasses recombinant Marek's Disease Virus that contains deletions and/or mutations in genes and gene regions essential for viral replication or some other stage of the viral life cycle, including initiation of infection and packaging of viral particles. In accordance with this aspect of the present invention, the deletions and/or mutations of the MDV genome are sufficient to eliminate or decrease expression of the essentional gene product and/or eliminate or decrease the activity of the essentional gene product. Examples of MDV genes that may be targeted include, but are not limited to, gH, gB, gD and the capsid gene. In accordance with this aspect of the invention, essential regions of the MDV genome are targeted in an attempt to generate a recombinant MDV with an attenuated phenotype.

Another embodiment the present invention encompasses recombinant Marek's Disease Virus that contains deletions and/or mutations in essential or non-essential regions of the MDV genome. Such regions in the MDV genome may be substituted with any heterologous nucleotide sequence to create a chimeric MDV vector. Virtually any heterologous gene sequence can be constructed into the MDV vectors for use in vaccines. In accordance with this aspect of the present invention, the heterologous gene sequence may encompass a gene product that may serve to boost or activate the host's cellular and/or humoral immune response, or a gene product that encodes an epitope that induces a protective immune response to any variety of pathogens, or antigens that bind neutralizing antibodies. For example, heterologous gene sequences that can be constructed into the chimeric vectors of the invention for use in vaccines include, but are not limited to, sequences derived from other serotypes of MDV, New Castle Disease Virus (NDV), Infectious Bursal Disease Virus (IBDV), Infectious Bronchitis Virus (IBV), Chicken Anemia Virus (CAV), Infectious Laryngotracheitis Virus (ILV), Avian Leukosis virus (ALV), Reticuloendotheliosis Virus (RV) and Avian Influenza Virus (AIV) (see, Fields et al. (ed.), 1991, Fundamental Virology, Second Edition, Raven Press, New York, incorporated by reference herein in its entirety).

Insertion of a foreign gene sequence into the MDV genome can be accomplished by either a complete replacement of the viral coding region with the foreign gene or by a partial replacement. Complete replacement would probably best be accomplished through the use of PCR-directed mutagenesis. Briefly, PCR-primer A would contain, from the 5' to 3' end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the MDV gene; and a stretch of nucleotides complementary to the carboxy-terminus coding fragment of the foreign gene product. PCR-primer B would contain from the 5' to 3' end: a unique restriction enzyme site; a stretch of nucleotides complementary to a MDV gene; and a stretch of nucleotides corresponding to the 5' coding fragment of the foreign gene. After a PCR reaction using these primers with a cloned copy of the foreign gene, the product may be excised and cloned using the unique restriction sites. Digestion with the class IIS enzyme and transcription with the purified phage polymerase would generate a molecule containing the exact untranslated ends of the MDV gene with a foreign gene insertion.

It is understood that recombinant MDV includes, for example, substitutions, insertions, inversions, additions, and deletions to the nucleic acid sequence of Marek's Disease Virus, and any combination thereof, such as deletion mutants of Marek's Disease Virus in which non-essential or essential regions of the MDV genome are deleted or mutated so that these regions are not expressed, e.g., gene knock outs or missense mutations. Such variations can occur in nature or may be genetically engineered using conventional recombinant techniques to bring about such variation.

The production and manipulation of recombinant Marek's Disease Virus or fragments thereof are within the skill in the art and can be carried out according to recombinant techniques described, among other places, in Maniatis, et al., 1989, Molecular Cloning, A Laboratory Manual, Cold Spring Harbor Laboratory Press, Cold Spring Harbor, N.Y.; Ausubel, et al., 1989, Current Protocols in Molecular Biology, Greene publishing Associates and Wiley Interscience, N.Y.; Sambrook et al., 1989, Molecular Cloning, A Laboratory Manual, 2d. ed., Cold Spring Harbor Laboratory Press, Cold Spring Harbor, N.Y.; Innis et al. (eds.)1995, PCR Strategies, Academic Press, Inc., San Diego; and Erlich (ed), 1992, PCR Technology, Oxford University Press, New York, all of which are incorporated herein by reference in their entireties.

The preparation of various recombinant Marek's Disease Virus and Marek's Disease Virus vectors using recombinant techniques is known. For example, U.S. Pat. No. 5,231,023, issued Jul. 27, 1993, describes a Marek's Disease Virus Viral vector prepared by insertion of a heterologous gene into a nonessential region of the DNA genome of MDV.

The invention also encompasses the DNA expression vectors that contain any of the foregoing coding sequences operatively associated with a regulatory element that directs expression of the coding sequences and genetically engineered host cells that contain any of the foregoing coding sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression. In a preferred embodiment of the present invention, regulatory elements are utilized which are active in quail cell lines or are induced by MDV, which as demonstrated by the Applicants, include: the promoter elements of gD of Herpes Simplex Virus-1 (HSV-1), the gG promoter elements of ILTV, the gC promoter elements of ILTV, the gX promoter elements of PRV, the SV40 promoter, the CMV promoter and the RSV promoter.

The MDV genomes or fragments thereof, may be produced by recombinant DNA technology using techniques well known in the art. Methods which are well known to those skilled in the art can be used to construct expression vectors containing MDV coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding MDV gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

In accordance with the present invention, the term 'MDV vector' encompasses an expression vector containing the appropriate regulatory sequences necessary for expression of one or more functional polypeptides, such as antigens. Examples of MDV vectors of the present invention include those that express the MDV genome or fragments thereof under the control of MDV regulatory elements or heterologous regulatory elements designed to enhance expression of the MDV genome in the packaging cell line. In a preferred embodiment of the present invention, regulatory elements are utilized which are active in quail cell lines or induced by MDV which as demonstrated by the Applicants, include the promoter elements of gD gene of Herpes Simplex Virus-1 (HSV-1), the gG promoter elements of ILTV, the gC promoter elements of ILTV, the gX promoter elements of PRV, the SV40 promoter, the CMV promoter and the RSV promoter.

The present invention also encompasses recombinant MDV vectors that result in virus particles with an attenuated phenotype, an example of which, is a recombinant MDV from which an essential gene has been mutated and/or deleted resulting in a replication defective MDV. The MDV genome or fragments thereof may encompass the nucleotide sequences of the wild-type MDV, the nucleotide sequences of genetically altered MDV or fragments thereof, including deletions of essential gene regions or the insertion of heterologous sequences. A preferred embodiment of this aspect of the invention is a recombinant MDV genome that has been deleted of the gH gene in its entirety or a large enough fragment thereof to prevent the expression of the gH gene product, or in which the gH gene has been mutated, e.g., a missense mutation so as to prevent expression of the gH gene product. Yet another preferred embodiment of this aspect of the invention encompasses is a recombinant MDV genome which has been deleted of the capsid gene in its entirety or a large enough fragment thereof to prevent the expression of the capsid gene product, or in which the capsid gene has been mutated, e.g., a missense mutation so as to prevent expression of the capsid gene product.

It is understood that MDV also encompasses recombinant MDV comprising a heterologous gene or genes incorporated into an insertion region located within the nucleic acid sequence of the genome of MDV. In a preferred embodiment of this aspect of the invention, the MDV genome is engineered to express an antigenic peptide of one or more of the three serotypes of MDV, so as to result in a multivalent vaccine to be administered to avians to confer a more complete protective effect against infection with MDV. For example, the MDV genome of a serotype 1 of MDV may be engineered to further encode the antigenic determinants of the gB gene product of serotypes MDV 2 and 3. In yet another embodiment, the heterologous genes and gene fragments may encode antigens of other avian disease causing agents. Methods for preparing recombinant Marek's Disease Virus containing heterologous genes and fragments are within the skill in the art and can be carried out according to recombinant techniques described in Maniatis et al. and other references noted above.

In yet another embodiment of the present invention, the MDV vector may be engineered to contain the nucleotide sequences of recombinant MDV and one or more heterologous genes which encode antigens for MDV or other avian disease causing agents, such as ALV. In yet another embodiment, the heterologous genes and gene fragments may encode antigens of other avian disease causing agents. In yet another embodiment, the MDV vectors of the present invention may be engineered to encode heterologous proteins which are known to boost the avian cellular immune response, thus enhancing the overall protective effect of the administered vaccine.

The MDV and heterologous genes which are engineered into the MDV vectors of the present invention may be done so using recombinant techniques within the skill of those in the art, can be expressed in the continuous avian cell lines of the present invention, and once formulated into an appropriate form and administered to avians elicit an immune response to both the recombinant Marek's Disease virus and/or the heterologous gene products. An adequate and functional promoter should be linked to the heterologous gene so that the MDV vector is capable of expressing the heterologous gene. The promoter may be any eucaryotic, procaryotic, or viral promoter capable of directing transcription in cells infected with the recombinant MDV vector. The preparation and use of such promoters is known and can be carried out according to recombinant techniques described in Maniatis et al., and the other references cited above.

The present invention encompasses processes for producing MDV and MDV vectors by infecting and transfecting and culturing continuous avian cell lines, such as for example feline kidney cells and quail cell lines, which are capable of producing MDV or useful in the production of MDV vectors. The MDV produced in such cell lines that can then be isolated using isolation techniques known to those of skill in the art. By "infection" or "transfection" is meant the DNA transfer of virus or fragments thereof into cells. Methods for gene transfer into cells is within the skill in the art as described, for example, by Watson et al., 1992, Recombinant DNA, 2nd edition, W. H. Freeman and Company N.Y.

The present invention relates to continuous avian cell lines, in particular quail muscle myoblasts, that efficiently support the growth and productive infection of Marek's Disease Virus at high titers. The present invention also encompasses continuous quail muscle myoblasts that are engineered to express MDV gene products that are required for viral replication. In accordance with this aspect of the invention, such cell lines are termed "complementation cell lines" since they complement the essential viral genes and gene regions that are deleted or mutated in the recombinant MDV vectors.

The complementation cell lines of the present invention may be engineered to express any gene or gene region which has been deleted from a recombinant MDV vector. In accordance with this aspect of the invention, the cell lines may be engineered to express MDV gene products, including, but not limited to, the gH, gB, gD or capsid proteins. The cells lines may be engineered to express the MDV gene products transiently or stably under the control of constitutively active or inducible regulatory elements. In a preferred embodiment of the present invention, regulatory elements are utilized which are active in quail cell lines or induced by MDV which as demonstrated by the Applicants, include the promoter element of gD of HSV-1, the promoter elements of gG and gC of ILTV, the promoter element of gX of PRV, the SV40 promoter elements, the CMV promoter element and the RSV promoter elements.

In a particularly desirable approach, cells engineered to express all MDV viral genes may result in the production of infectious chimeric virus that contains the desired genotype, thus eliminating the need for a selection system. Theoretically, one can replace any one of the genes of MDV with a foreign sequence. However, a necessary part of this equation is the ability to propagate the defective virus (defective because a normal viral gene product is missing or altered). A number of possible approaches exist to circumvent this problem. In one approach, a virus having a mutant protein can be grown in cell lines which are constricted to constitutively express the wild type version of the same protein. By this way, the cell line complements the mutation in the virus. Similar techniques may be used to construct transformed cell lines that constitutively express any of the MDV genes. These cell lines that are made to express the viral protein may be used to complement the defect in the recombinant virus and thereby propagate it. Alternatively, certain natural host range systems may be available to propagate recombinant virus, i.e., avian cell lines. A third approach to propagating the recombinant virus may involve co-cultivation with wild-type virus. This could be done by simply taking recombinant virus and co-infecting cells with this and another wild-type MDV virus (preferably a vaccine strain). The wild-type virus should complement for the defective virus gene product and allow growth of both the wild-type and recombinant virus.

For long term, high-yield production of recombinant proteins, stable expression is preferred. For example, avian cell lines which stably express the MDV gene products may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines, such as the gD and gH expressing cell lines as described herein. In yet another embodiment of the present invention, the DNA sequence encoding the recombinant MDV and regulatory element may be delivered to a host cell and introduced into the host genome via homologous recombination the DNA sequence encoding the recombinant MDV and regulatory element may be delivered to a host cell and introduced into the host genome via homologous recombination, a technique well known to those of skill in the art and described e.g. in Chappel, U.S. Pat. No. 4,215,051; Skoultchi, WO91/06667, each of which is incorporated by reference in its entirety.

A number of selection systems may be used, including but not limited to the herpes simplex virus thymidine kinase (Wigler, et al., 1977, Cell 11:223), hypoxanthine-guanine phosphoribosyltransferase (Szybalski & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt- cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147). In another embodiment of the present invention, a green fluorescence gene, as described herein, can be used to detect expression of the target gene.

The present invention also encompasses the continuous avian cell lines infected with MDV or a MDV vector. The avian cell line for infection or transfection with MDV is characterized as a continuous cell line free of avian viruses. Preferably, the avian cell line is a quail cell line. These cell lines may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

The preferred avian cell line of the present invention is a quail cell line, and more preferably a quail muscle myoblast cell line. Any quail muscle myoblast cell line may be utilized in accordance with the present invention, for example, quail cell line deposited on Nov. 24, 1998 with the American Type Culture Collection (ATCC) designated ATCC CRL 12599. In a preferred embodiment the present invention does not encompass the quail cell line designated QT35 to culture MDV serotypes 2 or 3. In a preferred embodiment, the quail cell line designated QM7 is used to culture the MDV vectors and viruses of the present invention. In yet another preferred embodiment of the present invention, the quail cell line designated QM7 infected with MDV strain 652, deposited with the ATCC on Nov. 24, 1998 designated ATCC-CRL 12600.

Avian cell lines, for use in the present invention can be cloned using known cell culture techniques familiar to one skilled in the art. The cells can be cultured and expanded from a single cell using commercially available culture media under known conditions suitable for propagating cells.

For example, the cell lines of the present invention kept frozen until use, can be warmed at a temperature of about 37° C. and then added to a suitable growth medium such as DMEM/F-12 (Life Technologies, Inc.) containing 3% fetal bovine serum (FBS). The cells can be incubated at a temperature of about 37° C. in a humidified incubator with about 5% $CO_2$ until confluent. In order to passage the cells, the growth medium can be removed 0.05% trypsin and 0.53mM EDTA added to the cells. The cells will detach and the cell suspension can be collected into centrifuge tubes and centrifuged into cell pellets. The trypsin solution can be removed and the cell pellet resuspended into new growth medium. The cells can then be further propagated in additional growth vessels to a desired density.

In accordance with the present invention, a continuous cell line encompasses immortalized cells which can be maintained in vitro for at least 15 passages.

Infection and transfection can occur by co-cultivation with MDV-infected cells where the MDV is non-recombinant, recombinant, genetically engineered or is an MDV vector. The cells used for co-cultivation can be MDV-infected cells such as CEF cells or DEF cells, lymphoblastoid cells, peripheral blood mononuclear cells, CHCC-OU2 cells, quail cells, and clones of quail cells described in the Examples. Alternatively, avian cell lines may be infected with MDV by introduction of purified MDV DNA or DNA from MDV-infected cells into the avian cell lines using methods which are known to those of skill in the art, such as calcium phosphate coprecipitation, DEAE dextran, polybrene, lipofectin, and electroporation. Preferably, DEF or CEF MDV-infected cells are used to infect the continuous avian cell lines of the present invention. The cultivation of MDV-infected CEF, DEF, lymphoblastoid, peripheral blood mononuclear cells, CHCC-OU2 cells and quail cells are known to those of skill in the art.

For example, the avian cell lines can then be infected with MDV by growing the cells to about 50 to about 80% confluency, and adding cells infected with MDV to the semi-confluent cells. The cells can then be incubated at a temperature of about 37° C. for about one week, with medium exchange every 2 to 3 days. The cells can then be split by trypsinization as described above. Infected cells can be monitored by cytopathic effect (CPE) and formation of infected cell foci and indirect fluorescent antibody (IFA) using an MDV specific antibody. MDV-specific antibody can be produced using known monoclonal hybridoma techniques [Goding, James W., Monoclonal Antibodies: Principals and Practice, second edition, Academic Press (1986); Harlow et al., Antibodies, a Laboratory Manual Cold Spring Harbor Laboratory (1988)]. A frozen stock of the MDV-infected cells can then be stored until ready for use.

The present invention also relates to processes for production of vaccines comprising the MDV produced by infecting continuous cell lines, such as for example quail cell lines, and culturing infected cell lines to produce antigens useful as vaccines against MDV. The MDV infected cells can then be used as vaccines against MDV or the cell-free MDV isolated from the cells can be used as vaccines.

The present invention further relates to processes for producing vaccines comprising the MDV produced by transfecting or infecting continuous avian cell lines, such as quail cell lines, with an MDV vector comprising MDV and the genes of one or more heterologous proteins or polypeptides, that is capable of expressing heterologous genes in addition to MDV, which are useful against avian disease causing agents other than MDV.

Furthermore, the invention relates to processes for producing vaccines produced by transfecting continuous avian cell lines with an MDV vector comprising replication-defective MDV and the genes or parts thereof of one or more heterologous proteins or polypeptides, that is capable of expressing heterologous genes in addition to MDV, which are useful against avian disease causing agents other than MDV.

Furthermore, the invention relates to processes for producing vaccines produced by transfecting continuous avian cell lines with an MDV vector comprising replication-defective MDV and the genes thereof of one or more heterologous proteins or polypeptides, which is capable of expressing heterologous genes in addition to MDV, which are useful against avian disease causing agents in addition to MDV, which are useful against avian disease causing agents other than MDV. Examples of other avian disease causing agents which may be useful for the production of vaccines and which are produced using the processes of the present invention include New Castle Disease Virus (NDV), Infectious Bursal Disease Virus (IBDV), Infectious Bronchitis Virus (IBV), Chicken Anemia Virus (CAV), Infectious Laryngotracheitis Virus (ILV), Avian Leukosis Virus (ALV), Reticuloendotheliosis Virus (RV) and Avian Influenza Virus (AIV) (see, Fields et al. (ed.), 1991, Fundamental Virology, Second Edition, Raven Press, New York, incorporated by reference herein in its entirety). MDV produced using the process of the present invention containing one or more heterologous proteins and polypeptides can serve as a monovalent or multivalent vaccine. Such vaccines can be prepared by methods well known to those skilled in the art of preparation of vaccines.

In accordance with the present invention, vaccine preparations comprising cell lines or components thereof e.g., cell lysates should be tested to ensure that the cell lines are free of other viruses and pathogens. In particular, cell lines to be formulated into vaccines to be administered to animals, such as avians, should be tested for the presence of retroviruses, such an assay can be carried out using methods known to those of skill in the art, such as a reverse transcriptase assay (Boehringer Mannheim). In addition, the cell lines may be assayed for the presence of avian pathogens using commercially available assays.

The present invention further comprises methods of administering MDV vaccines and MDV vector-produced vaccines to animal for the protection against infection with MDV. The MDV-expressing MDV and/or one or more heterologous proteins or polypeptides including those which would serve to boost the avian immune response or proteins or polypeptides of avian disease causing agents can be used to vaccinate animals, such as chickens and turkeys susceptible to such disease causing agents. Vaccination with the MDV or other antigens produced using the process of the present invention results in a protective immune response so that the inoculated animals will be protected from subsequent infection by those disease causing agents.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In this regard, the use of genetically engineered MDV (vectors) for vaccine purposes may desire the presence of attenuation characteristics in these strains. The introduction of appropriate mutations (e.g., deletions) into the templates used for transfection may provide the novel viruses with attenuation characteristics. For example, specific missense mutations that are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication within the host. When used as a vaccine, the recombinant virus would go through limited replication cycle(s) and induce a sufficient level of immune response but it would not go further in the animal host and cause disease. Recombinant viruses lacking one or more of the MDV genes or possessing mutated MDV genes would not be able to undergo successive rounds of replication. Defective viruses can be produced in cell lines which permanently express such a gene(s). Viruses lacking an essential gene(s) will be replicated in these cell lines but when administered to the animal host will not be able to complete a round of replication. In addition to non-infectious viral particles produced, such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. In yet another embodiment of the present invention, subunit vaccines comprising the antigenic determinants of MDV or heterologous viral antigenic determinants may be formulated as vaccines. The advantage of such preparations is that they contain native proteins and do not undergo inactivation by treatment with formalin or other agents used in the manufacturing of killed virus vaccines.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or—propiolactone, and pooled. The resulting vaccine is usually inoculated intramuscularly.

In yet another embodiment of the present invention, nucleotide sequences encoding recombinant MDV with an attenuated phenotype or nucleotide sequences encoding recombinant MDV and/or heterologous antigenic determinants may be formulated as vaccines. In accordance with this embodiment, vaccine compositions can comprise DNA encoding recombinant MDV having an attenuated phenotype and/or containing MDV and/or heterologous antigenic determinants operatively associated with a regulatory sequence that controls gene expression. In accordance with is aspect of the present invention, the DNA of interest is engineered into an expression vector under the control of regulatory elements that promote expression of the DNA i.e., promoter or enhancer elements. In one preferred embodiment, the promoter element may be cell-specific and permit substantial transcription of the DNA only in predetermined cells. The DNA may be introduced directly into the host either as naked DNA (U.S. Pat. No. 5,679,647 incorporated herein by reference in their entirety) or formulated in compositions with other agents which may facilitate uptake of the DNA including viral vectors, or agents which facilitate immunization, such as bupivicaine and other local anesthetics (U.S. Pat. No. 5,593,972 incorporated herein by reference in their entirety), saponins (U.S. Pat. No. 5,739, 118 incorporated herein by reference in their entirety) and cationic polyamines (published international application WO 96/10038 incorporated herein by reference in their entirety.

Inactivated viruses may be formulated with a suitable adjuvant in order to enhance the immunological response. Such adjuvants may include, but are not limited to, mineral gels, e.g., aluminum hydroxide; surface active substances such as lysolecithin, pluronic polyols, polyanions; peptides; oil emulsions; and potentially useful adjuvants such as BCG and Corynebacterium parvum.

The cell lines and components thereof of the present invention may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The patient to which the vaccine is administered is preferably an avian, most preferably a fowl, such as a chicken or turkey, a non-avian animal including, but not limited to, cows, horses.

The vaccine formulations of the invention comprise an effective immunizing amount of the cell lines and components thereof of the present invention and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include, but are not limited to, saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is more preferably sterile. The formulation should split the mode of administration.

The composition, if desired, can also contain minor amounts of wetting or emulsifying agents, or pH buffering agents. The composition can be a liquid solution, suspension, mulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixer prior to administration.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed. The immunopotency of the MDV vaccine can be determined by monitoring the immune response in test animals following immunization with the vaccine, e.g., generation of a humoral (antibody) response and/or cell-mediated immunity may be taken as an indication of an immune response. Effective doses (immunizing amounts) of the vaccines of the invention may be extrapolated from dose-response curves derived from animal model test systems. The following examples further illustrate, but do not limit the present invention.

EXAMPLE 1

QM7 Cells Can Efficiently Support MDV Infection

In this study QM7 cells are Japanese quail muscle myoblasts (ATCC CRL 12599), derived from the QT6 fibrosarcoma cell line, that were identified as a cell line which can support MDV-1 growth at high titers.

The 652 and 584A isolates of MDV are very virulent plus isolates of MDV [Witter, R. L., Avian Dis., V. 41, pp 149–163 (1997)]. QM7 cells were infected with MDV infected DEF inoculum, 652/DEF at cell culture passage 11. Productive infection of the MDV-1 (strain 652) was monitored by CPE (cytopathic effect) by quantifying formation of foci and by detecting MDV viral proteins (gB & pp38) expression in IFA assay (FIG. 1). Large and intensely stained infected foci were detected. The infection can be maintained by inoculating 652/QM7 infected cells into seeded (50–60% confluence) uninfected QM7 cells, respectively. 652/QM7 infected foci are large enough to be visually detectable without requiring antibody staining. The QT6 fibrosarcoma cell line was also tested for its ability to support a productive MDV infection. However, the QT6 cell line did not prove to be a very efficient host for the growth of MDV.

The results indicate that QM7 cells can efficiently support infection by MDV-1, however, in order to further characterize and optimize MDV-1 infection of QM7 cells, six different growth conditions (two serum concentrations, three split ratios) were tested. The results are summarized below.

TABLE 1

The Titration of 652/QM7 cell passage 3 in DMEM/F12 medium

| Serum conc. | Split ratio | TCID50/ml |
|---|---|---|
| 3% | 1:2 | 3.75 |
| 3% | 1:5 | 3.50 |
| 3% | 1:10 | 3.75 |
| 10% | 1:2 | 1.75 |
| 10% | 1:5 | 2.00 |
| 10% | 1:10 | 1.75 |

TABLE 2

The titration of 652/QM7 cells at passage 7 and 10

| Medium | Serum Conc. | Split Ratio | TCID50/mp7 | TCID50/ml10 |
|---|---|---|---|---|
| DMEM/F-12 | 3% | 1:5 | 4.2 | 4.7 |
| DMEM/F-12 | 3% | 1:10 | 4.2 | 4.7 |
| DMEM/F-12 | 3% | 1:20 | 3.2 | 3.7 |
| DMEM/F-12 | 1% | 1:20 | 4.2 | 4.2 |
| DMEM/F-12 | 1% | 1:10 | 4.2 | 3.7 |
| DMEM/F-12 | 1% | 1:20 | 3.2 | 3.2 |
| Optimem | 2% | 1:10 | 4.2 | 4.7 |

These results indicate that the best growth conditions for 652/QM7 infection is to culture the infected cells in DMEM/F-12 with 3% fetal bovine serum with split ratio 1:10. Titers clearly fell when split ratios were extended to 1:20. The titers remained consistent from passage 7 to passage 10.

Reverse Transcriptase Assay On QM7 and 652/QM7 Cells

Cell lines were tested for reverse transcriptase activity using a commercially available Non-Radioactive Reverse Transcriptase (RT) Assay (Boehringer Mannheim). Cell lysate, clarified supernatant, and untracentrifuged pellet were prepared from DEF, 652/DEF, QM7, 652/QM7 and NYU cells (as a positive control). All samples were done in triplicate and results represent two RT assay. HIV-1 RT was used to construct the standard curve.

| Cell line/RT Activity (ng/well) | Lysate | Supernatant | Pellet |
|---|---|---|---|
| NYU | 0.819 | 0.003 | 1.945 |
| DEF | −0.144 | −0.155 | −0.455 |
| 652/DEF | −1.455 | −4.456 | −0.455 |
| QM7 | −0.142 | −0.155 | −0.155 |
| 652/QM7 | −0.456 | −0.458 | −0.456 |

NYU cells was chosen as an internal positive control for its known retroviral RT activity. As these results demonstrate, ultracentrifuge pellet and cell lysates obtained from NYU cells provide a strong positive result for RT activity. QM7, 652/QM7, DEF and 652/DEF cells were clearly negative for reverse transcriptase active in this assay, which is sensitive to at least 20 picograms. These results indicate that all four cell lines do not harbor any retroviral particles.

Avian extraneous virus testing

QM7 cells were also test for the presense of any avian pathogens using the U.S. Department of Agriculture test 9CFR 113.37 "Detection of Pathogens by the Chick Embryo Inoculation Test", and were found to free of any avian pathogens. In short, QM7 cell suspension was infected into the chick embryo. The presence of any avian extraneous virus would lead to the damage of the chick embryo.

Transfection of MDV-1 (652) DNA Lead To Productive Lytic Infection in QM7 Cells

Naked DNA was isolated from 652/QM7 infected cells and transfected with uninfected QM7 cells using a CaPO4 transfection method (ClonTech kit). After 7 days incubation with a medium change every 2–3 days, many infected foci can be seen on the transfection plate. These foci are indistinguishable from the foci established by cocultivation with 652/QM7 infected cells. This result demonstrates, un-equivocally, that MDV-1 can replicate and grow productively in QM7 cells, ruling out the possibility that the 652/QM7 foci result from contaminated inoculum.

EXAMPLE 2

Different Promoter Activities in QM7 Cells

The following experiments were conducted to demonstrate which promoters are active in QM7 cells and further, to identify promoters which are activated or induced in the course of MDV infection. Luciferase reporter constructs (pGL3 based, Promega) which contain different promoters (pSV40+enhancer, PSV40, pCMV, pRSV) were transfected into QM7, and DEF cells, respectively. Seventy-two hours later, cell lysate was collected and luciferase activity was assayed with different dilutions.

TABLE 3

Luciferase Activities of different promoters in QM7 & DEF cells

| Cells | Promoters | 1:10 | 1:100 | 1:1000 | 1:10000 |
|---|---|---|---|---|---|
| QM7 | pSV40 + enhancer | 9999 | 9999 | 1374 | 48.19 |
|  | pSV40 | 9999 | 3658 | 246.9 | 8.34 |
|  | pCMV | 9999 | 9999 | 802.9 | 28.77 |
|  | pRSV | 9999 | 9999 | 1316 | 44.42 |
|  | no promoter | 1673 | 153.5 | 8.53 | 0.379 |
| DEF | pSV40 + enhancer | 9999 | 2287 | 145.7 | 3.217 |
|  | pSV40 | 3832 | 347.2 | 19.36 | 0.533 |
|  | pCMV | 9999 | 1286 | 82.76 | 2.236 |
|  | pRSV | 9999 | 2327 | 162.8 | 4.301 |
|  | no promoter | 97.3 | 8.09 | 0.586 | 0.022 |

These results suggested that these different promoters (pCMV, pRSV, pSV40 and pSV40+enhancer) are very active in QM7 cells. Furthermore, pRSV is an especially strong promoter in these avian cells.

Various MDV-1 viral inducible promoter constructs, were transfected into 652/QM7 in order to test the promoter strength under inducible conditions. Luciferase activity, generated from the luciferase reporter gene, was measured. In addition to the pCMV promoter which was used as a control, five different viral promoters were tested: gH gene promoter elements of MDV-1 (MD5 strain); the promoter elements of the gG and gC gene of ILTV; the gX gene promoter elements of PRV and the gD promoter of HSV-1.

TABLE 4

Activity of different promoters in MDV infected QM7 cells

| Promoters | Sources | QM7 control 1:100 | 1:1,000 | 652/QM7 1:100 | 1:1,000 | Increasing Folds |
|---|---|---|---|---|---|---|
| pgH2 | MDV-1 | 19.69 |  | 36.53 |  | 2X |
| pgG | ILTV | 9999 | 34.8 | 9999 | 117.5 | 4X |
| pgC | ILTV | 79.58 |  | 278.4 |  | 4X |
| pgX | PRV | 761 | 1.092 | 4969 | 7.169 | 7X |
| pgD | HSV-1 | 44.12 |  | 517.2 |  | 10X |
| PCMV |  | 9999 | 9.62 | 9999 | 61.94 | 7X |

These results suggested that the promoter pgD from HSV-1 is highly induced and should be active as a viral inducible promoter in MDV infection of QM7 cells. The pCMV promoter is also active in viral infected QM7 cells.

EXAMPLE 3

In vivo Pathogenicity Study

652/QM7 infected cells were tested for their ability to cause Marek's Disease in chickens in an in vivo pathogenicity study.

Five groups of 30 chicks each at 1 day of age were inoculated intraperitoneally with (1) a mixture of uninfected QM7 cells; (2) 652-infected QM7 cells at cell culture passage 3; (3) 652-infected QM7 cells at cell culture passage 3; (4) 652-infected QM7 cells at cell culture passage 7; and (5) 652-infected QM7 cells at cell culture passage 7. The birds were inoculated with either 250 or 750 TCID50 of MDV per chick. Titration of virus was determined using the TCID50 method on monolayers of secondary DEF cells fixed with 80% acetone 6–8 days following infection and examined by IFA as described above.

Infected and uninfected cells were grown at 37° and 5% CO2 in humidified incubators in DMEM/F-12 (Life Technologies) supplemented with antibiotics and appropriate amounts of fetal bovine serum (3% for infected cells and 10% for uninfected cells).

Birds were necropsied if they died during the study and examined for signs of MDV infection. Kidney, spleen, liver and brain were harvested for histological evaluation from surviving birds.

All chickens injected with 652 infected cells developed classical signs of very virulent MDV, and the majority of these birds died of MD. The uninfected cell groups did not develop any signs of MD for the duration of the experiment (8 weeks of age). The results are shown in Table 5.

TABLE 5

In vivo Pathogenicity of 652/QM7 cells

| Samples | TCID50 | Mortality | Lesions | % Positive |
|---|---|---|---|---|
| QM7 | N/A | 1/30 | 0/15 | 0 |
| 652/QM7p3 | 750 | 28/30 | 30/30 | 100 |
| 652/QM7p3 | 250 | 22/30 | 28/30 | 100 |
| 652/QM7p7 | 750 | 22/30 | 28/30 | 93/5 |
| 652/QM7p7 | 250 | 27/30 | 29/30 | 96.5 |

Histopathological evaluation of tissues (kidney, spleen, liver, heart and brain) revealed lesions which were consistent with Marek's disease in surviving birds from the infected groups. No such lesions were seen in birds from the cell control or negative control groups.

These in vivo experiments demonstrate that MDV-1 (652) grown in QM7 cells are very virulent, confirming that QM7 cells are a good host to propagate infection of the MDV-1 virus at high titers.

EXAMPLE 4

Preparation of pCR3.1gH Construct

The 2.6kb Glycoprotein H (gH) gene from Marek's Disease Virus strain MD5 was isolated 3 by polymerase chain reaction (PCR) and cloned into pCR2 TA cloning (TA cloning vector, available from Invitrogen Inc., U.S.A., catalogue number K2000–1) by polymerase chain reaction (PCR) using a commercially available PCR regent system (GIBCO-Life Technologies, cat No. 10198-018), using an upper PCR primer 5'-GGGGG TACCA AGUG CATTG GATGG CTACA TA-3' (SEQ ID NO: 3) and a lower PCR primer 5'-GGGGC TAGCT TAAAG ATCGT CGTAC AGGCT CAA-3 (SEQ ID NO: 4). The gH gene can be sequenced using known techniques. The sequence for the gH gene is described by Scott et al., J. Gen. Virol. vol. 74. pp.1185–1190. (1993).

The MDV gH gene was then subcloned into pCR3.1 vector (available from Invitrogen Inc., U.S.A., Catalog Number K3000-01) utilizing the Kpnl and Xhol sites in the multiple cloning site (see FIG. 2). The vector pCR3.1 is a eukaryotic expression vector containing cytomegalovirus (CMV) immediate-early promoter for efficient mammalian expression and the neomycin resistance gene to allow positive selection for cells that contain the vector. The vector pCR3.1 is characterized by the following: CMV promoter bases 1–596; putative transcriptional start bases 520–625; 17 promoter/priming site bases 638–657; multiple cloning site bases 670–785; pCR3.1 reverse priming site bases 797415; BGH polyadenylation site bases 796–1010; ColEl oring bases 1100–1773; SV40 promoter and origin bases 3178–3515; pGreenLantern-2 plasmid, available from GIBCO-Life Technologies. U.S.A (see FIG. 5). The 5' flanking region of MDV-1 gH is available from GeneBank, U.S.A. contains the TK gene at position 894 to 1925. The pGreenLantern-2 plasmid has the gene encoding for the jellyfish green fluorescence protein (gfp) which is used as the marker protein in the process of generating gH-deleted recombinant virus. The Nsil site of pGreenLantern-2, upstream of the CMV promoter for the green fluorescence protein gene, is treated with T4 polymerase to create a blunt-end for ligating with the 5' gH flanking region containing Pme 1 ends.

A plasmid was obtained from Dr. Meihan Nonoyama of the Tampa Bay Research Institute FL, U.S.A. containing the MDV-1 BamH1 fragment F. which includes the gH 3' flanking region [Fukuchi et at, J. Virol. 102–109, (1984)]. The DNA sequence of about a 2.4 kb region (referred to herein as the 3"flanking region") is shown in SEQ ID No: 2. The MDV-1 gH 3' flanking region was obtained by PCR cloning (Upper primer: 5'- AAGAT TTTTC CCMG TCC-3' (SEQ ID NO: 5). Lower primer 5'-TCGTC GMTA ATGTG ATC-3') (SEQ ID NO: 6) and cloned into the above mentioned pGreenLantern-2 plasmid which has the MDV.1 5' flanking region inserted at the Nsil site. The 3 flanking region was inserted into the Nael site, downstream of the whole green fluorescence protein gene. (FIG. 6).

Stable Expression of gH and gD Proteins in QM7 Cells

QM7 cells which stably express either MDV gH or MDV gD were generated as described below. Plasmid constructs, pCR3 gH-HA and pCR3gD-HA (HA tag was added to the C-terminal of gH and gD genes for easy detection) were transiently transfected into QM7 cells. The expression of each glycoprotein was demonstrated by immunofluorescence assay (IFA) using anti-HA monoclonal antibodies (FIG. 3).

Further, plasmid constructs: pCR3gH-HA, pCR3gD-HA, were stably transfected into QM7 cells and pools of g418 resistant cells were obtained. Single cell clones were obtained by dilutions using 96 well plates. Expression of both gH-HA and gD-HA proteins was visualized in immunofluorescence assays using HA monoclonal antibodies. Moreover, cells were metabolically labeled with 35S (TransLabel, ICN) and cell lysates were immunoprecipitated with HA antibody. A band of about 9OkD was present only in those lysates obtained from cells transfected with the pCR3gH-HA construct. A broad band of about 50 Kd was present only in those lysates obtained from cells transfected with pCR3gD-HA (FIG. 4). The size of the gH and the expressed gd proteins from the pCR3 vector in QM7 cells correlates well with their predicted sizes. Thus, the results demonstrate that QM7 cells may be engineered to express MDV proteins required for viral replication. Several single cell clones have very abundant gH-HA protein expression. These cell lines are good candidates for complementing gH function. In addition, QM7 cells co-expressing both gH and gD proteins were established by co-transfecting both pCR3gH-HA and pCR3gD-HA into QM7 cells.

EXAMPLE 5
Recombinant MDV with a gH Deletion
Preliminary identification of gH gfp+MDV-1 recombinant Plasmid construct, pGL2/5'–3' gfp, contains gfp (green fluorescence protein) as a selective marker (FIG. 6). It also contains the 5' and 3' flanking region of the gH gene for homologous recombination in order to replace the gfp for the gH gene. PGL2/5'–3' gfp was transfected into gH-HA producing cells which were infected with 652/QM7. Four days after transfection, the culture was passaged twice, each time with fresh gH-HA producing cells added. The whole infected culture was sorted by FACS for cells expressing gfp. The sorted cells, which are gfp+, were cultured in 2-well plates. After 6 days incubation, a few phenotypic foci could be seen. Moreover, these foci were green under u.v. light, suggesting that these are positive gfp+g-MDV-1 candidates.

Due to the cell-associated nature of MDV-1, it is a challenging task to purify gfp+gH recombinant away from its wild-type counterpart. However, after two culture passages, many foci no longer appeared green, indicating that the wild-type viruses are segregated out. Those cultures were FACS sorted one more time using gfp as selective marker, which resulted in the sorting of green foci indicating positive gfp+gH-MDV-1 clones. The gfp+gH-recombinant is being purified and will be further analyzed by PCR and Southern analysis.

In a second recombination step to remove the green fluorescence protein gene from the gH gene deleted virus, one can optionally insert heterologous genes from viruses other than MDV. Such as, for example, the chicken interferon gene, Newcastle disease virus, or infection bursal disease viruses etc., which can replace the green fluorescence protein gene. The presence of white virus plaques in contrast to parental green foci, contain the new recombinant MDV-1 virus in which the gH gene is deleted and the green fluorescence protein gene removed.

A number of references have been cited and the entire disclosure of which are incorporated herein by reference.

The present invention is not to be limited in scope by the specific embodiments described which are intended as single illustrations of individual aspects of the invention, and functionally equivalent methods and components are with in the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A method for producing a Marek's Disease serotype 1, serotype 2 and serotype 3 virus (MDV), wherein said Marek's Disease virus is a wild-type or naturally occurring mutant viral particle, or a recombinant viral particle, which comprises culturing a continuous quail muscle myoblast cell line QM7 which is infected or transfected with nucleotide sequences encoding the MDV.

2. The method of claim 1 wherein the nucleotide sequences encode a naturally ccurring MDV.

3. The method of claim 1 wherein the nucleotide sequences encode a recombinant MDV.

4. The method of claim 3 wherein the MDV is a recombinant molecule comprising the nucleic acid sequence of MDV and at least one heterologous gene inserted into said nucleic acid sequence of MDV.

5. The method of claim 3 wherein the MDV is a recombinant molecule comprising the nucleic acid sequence of MDV from which one or more genes, regulatory genetic elements, has been deleted.

6. The method of claim 5 wherein the deleted gene is essential for replication.

7. The method of claim 6 wherein the deleted gene is gH.

8. The method of claim 1 wherein the MDV is a virus used for the preparation of a vaccine capable of inducing protection against disease in avians.

9. The method of claim 1 wherein the MDV is MDV-1 strain 652.

10. The method of claim 9 wherein the cell line is ATCC CRL-12600.

11. The method of claim 1, wherein the QM7 cell line is ATCC CRL-12599.

* * * * *

SEQUENCE LISTING

```
<160> NUMBER OF SEQ ID NOS: 8

<210> SEQ ID NO 1
<211> LENGTH: 2023
<212> TYPE: DNA
<213> ORGANISM: Marek's disease virus

<400> SEQUENCE: 1
acggtctctg aacaagacgg gcgataatat tagccatgtt tcgcatagcc gtacctcccg      60
ttctctcctg attatttgaa aatgataaag tagccgtttt attacaagct atatgattcc     120
tcaaatccgt tacgttagca gacgcctttc cactgcgtcg ttgtatatgt atcgtgtttg     180
tattatgacg ttttaaaatt ttatgagtgt cagttatccg tgctttatag tcagacgcgg     240
tcgccaatat agagcatagt ctatgaaaat cagtcactat gtgccttttc tttaggcaca     300
tcacatgtag aacagacagt tttcgtcttg ctacaaatac taacattgga caaataacga     360
tacaatctga tccttgaggc gcaatttgcc caatcagaga tttggaatcc aataactgct     420
ttatgccggt gagtctttgt tcatgtttac tgcgtgtctt caggttacga gaaaatttgc     480
aagtttttag ttctagaatg acgcatactc catcacagcc tacttcccac aaatcacgag     540
gcaacttaaa catgcaaata caatccggtc tacgtcgttc taggtttact tcgaagacca     600
atcgaaaatc cgtcaactgt ttaaatacat ctaataccat gaccttccca aaaattttgg     660
caaagcttct ccccggccaa tcatacacct gagatcctag acacatcgct tctgcataaa     720
gccgtttgta aaagcgatcg tgacatcgaa caccagccgc taaacgtcgc tttctaagga     780
cattcgtatt tacatgccgt ttgaaatttc gagtgctact aacctgtctg cgatatcttt     840
tgagtacgtt cttctctccc attgaacatg tcggagccac aatcgtggtc ggtaatggca     900
tctcagatga catctgcaca gctcatacgt gtatacctcg atggatcaat gggtataggt     960
aaaacgtcaa tgttgaatga gataccgacg cactctttaa tgggagtacc cgtactaaag    1020
gttttcgaac ctatgaaata ctggcggtat tattttactg atttggtcac gaccgtaaat    1080
```

-continued

| | | | | |
|---|---|---|---|---|
| gatacatgtg | atcgtcgtcg | caggggagag | ttttctttat | ttcaatctag catgattgta | 1140 |
| acagctttac | aatcaaagtt | tgcagatccc | tatcttgtat | ttcatgagcg cttatcgtcg | 1200 |
| aagtgtcatc | gcataacagg | aacacgtggc | aatccatcgc | ttatattaat tctagatcga | 1260 |
| catcccatat | ccgctaccgt | atgttttccc | attgctcgac | atttaactgg agattgttcc | 1320 |
| ttggagatgc | taattagtat | gataataagg | ttgccccagg | aaccgccagg atgcaacttg | 1380 |
| gtgattgtcg | atctacatga | cgaaaaggag | catgttagcc | gtctatcttc acggaatagg | 1440 |
| accggcgaga | aaacagatct | actaatgctc | agggcactta | atgcagtgta ttcctgttta | 1500 |
| gtagacacta | ttatgtacgc | aaatcatatt | tgtccctaca | gtaaggatga atgggaatct | 1560 |
| gaatggttgg | atctaccatg | gtttgataca | tcttggcca | aacgtttat aaacgaacct | 1620 |
| cgtactgatt | atcgcggtag | tagggtgtca | ttacaccata | cgcttttagc gatatttaag | 1680 |
| cggcgagaat | tatgtgccga | agatggtagc | ttatcaacaa | cgcatgcatg gatattgtgg | 1740 |
| ggattattaa | tgaaactgcg | gaacattaac | gtcgaacgat | ttaatattac tggcctgtcc | 1800 |
| acaacaaagt | gtgtagaatc | gttcatggat | actatgtcgg | agagattggt aacacatagt | 1860 |
| agctggaatg | atgccttcga | gattgaagct | gatgtactag | cctataataa agagatggct | 1920 |
| atgtaaaact | acccattcat | atcgcgcttc | tataattagc | ttgcccacat cacaatgatg | 1980 |
| cggcaatatt | gacttatatt | aagatagtaa | tttggcgtcc | tta | 2023 |

<210> SEQ ID NO 2
<211> LENGTH: 2236
<212> TYPE: DNA
<213> ORGANISM: Marek's disease virus

<400> SEQUENCE: 2

```
taaataaaga actttgggaa taacaagcta tgtatagaat ttatttcgcg tgaagatttt     60
tcccaagtcc gatcacattt caggtattac agcggtaata gatccatgca ttatgagggt    120
ttgacgtatt atctcgatta agaacatatt gtaatacacc cactgtttct caaacgagtg    180
tctatcaatg atataataca ttgatgtatc gactataata cccccaatgt tcaaaggctg    240
ataaaactga tatatctatg gccgcgcata gcaattctgc cgtatcttct cccaccgatt    300
ctcgtaacgc gacgtctatg ggatcaatgt ctttatatag accgtctaga ataagagcca    360
gtttacgtat cttgaggtcc tgtatagatt ttggtgcaga tgtttctgcc acatccaata    420
aagtagtctc gtctgcaaag gctgatggac taagaactcc atgttgctct tccaatgaag    480
aagtccagtt cacaactaat ttcagtaacc atgccaagaa ataaaatcct ctgaataaac    540
tgtttgtttc tgcaagacaa gtcggcatgg agtaggcatt ccccctcaat ggtagaggta    600
tgatgatcgc acaactcgcg aattaagtca taacaatttg gcagacgatt taatatatgt    660
atatactgaa gcaacaaaaa cttctgactg ggcgatatat ttttgttttc tggtccaact    720
ccaacaaaca tggatgcgtg tcttccaaat aaagcatttg aaatcatccc caactcactt    780
tgtataattt ccaggtcgga ttgagatcca ttctccgtat aagattagaa tttaaattga    840
gcatgttcat attaaaaacc gagtctactt tccagaagat ttcccataac ttatttagag    900
aagtagaggg tatacaagag ctggtatcgc aactccatat cttaaatacg ggtggtatat    960
atttgatttg taccaaagaa ctgaaccgag catgtttttt ccgttgtact ggatttgttt   1020
gttactgttc acgttcaatt taccccggct ccagccgtca tatcccatgc gcgttgcaca   1080
gtcgtcgtgt ttgcagcttt ctttgctgta actataacat cgactcgcct gccgaatatc   1140
tctgatgata atgcttctct aggagtggga atgccatcaa ataatccttc aacgaggtca   1200
```

-continued

```
ctcaaagact taggtaattc agtcaatctt gcacaagtta gcacaaatgc atcacgactg    1260
cactcatata ctaaatctga atatatgtcc gtgattatag ggaattcggg tatatgaatt    1320
gtacgatcat gtggaaaatc gtatgcggcc tgtatcgtta acccagaaat tgcatttgtc    1380
ggtaccatat actttgctat atccggatca tacgtttcca gacagagaag cccacaaagc    1440
tcacgttcac tgcatatacc atcacgactt aacacagcta tactatcgat gaacaattca    1500
tcttcatcgg aagaaaaagc ccacttcata cctctgcgaa gtaattctcg gcgaacatga    1560
gctgccaatg gtttggactg accaccacgt agaaccaacc caattttgc gagctctggt     1620 aataccatca tctatacagc ctgcctacag caaaaaacaa ccgccgcaaa aaaataccett   1680 tatatcccat tccgatacat aaaactggac attctataac gaaaacatgt ccgtatttaa    1740
tatccattga ctgtcctctc tggacgtaac ctatatcact gtagcgcaaa tccaatcctt    1800
gataacagca ttgcgttaat cactgggtgc acggattaac gtgtacgtat ttactgtcgc    1860
gtcatatgaa cgacaatgag cttgggtatg cagctcgtca ttgaacgcca tttgtggcaa    1920
agcaataagg gtctcagacc atcacattat tcgacgaatt gtactacata ggccaccect    1980 tgtttaacta tgtcaagcat ggatttggat actatgtcaa cagaagctaa tgaatatacc    2040 atcccectca tgaattgatg atggacgatc ggatacatgc gaaaactctt gggtcgtatt    2100
gaccactatc tgaggaatta gattgggatg atattatgca ctttctctta tttaggcgat    2160
atattttaca atccaacagc tatgacatac atcctcaaat cacccgtatg tttactctttt   2220 ggctatctac tttgtc                                                    2236

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3
gggggtacca agugcattgg atggctacat a                                     31

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 4
ggggctagct taaagatcgt cgtacaggct caa                                   33

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
aagatttttc ccaagtcc                                                    18

<210> SEQ ID NO 6
<211> LENGTH: 18
<212> TYPE: DNA
<213> ORGANISM: Artificial Sequence
<220> FEATURE:
```

-continued

```
<223> OTHER INFORMATION: Description of Artificial Sequence:  Primer

<400> SEQUENCE: 6
tcgtcgaata atgtgatc                                                18

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence:  pCR 3.1
      vector

<400> SEQUENCE: 7
taatacgact cactataggg agacccaagc tggctagcgt ttaaacttaa gcttggtac      59

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence:  pCR 3.1
      vector

<400> SEQUENCE: 8
tcgagtctag agggcccgtt taaacccgct gatcagcctc gactgtgcct tcta           54
```